US012217432B2

(12) United States Patent
El-Baz et al.

(10) Patent No.: US 12,217,432 B2
(45) Date of Patent: Feb. 4, 2025

(54) ASSESSMENT OF PULMONARY FUNCTION IN CORONAVIRUS PATIENTS

(71) Applicants: Ayman S. El-Baz, Louisville, KY (US); Ahmed Shalaby, Louisville, KY (US); Mohamed Elsharkawy, Louisville, KY (US); Ahmed Sharafeldeen, Louisville, KY (US); Ahmed Soliman, Louisville, KY (US); Ali Mahmoud, Louisville, KY (US); Harpal Sandhu, Louisville, KY (US); Guruprasad A. Giridharan, Louisville, KY (US)

(72) Inventors: Ayman S. El-Baz, Louisville, KY (US); Ahmed Shalaby, Louisville, KY (US); Mohamed Elsharkawy, Louisville, KY (US); Ahmed Sharafeldeen, Louisville, KY (US); Ahmed Soliman, Louisville, KY (US); Ali Mahmoud, Louisville, KY (US); Harpal Sandhu, Louisville, KY (US); Guruprasad A. Giridharan, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 421 days.

(21) Appl. No.: 17/685,493

(22) Filed: Mar. 3, 2022

(65) Prior Publication Data

US 2022/0284586 A1 Sep. 8, 2022

Related U.S. Application Data

(60) Provisional application No. 63/156,171, filed on Mar. 3, 2021.

(51) Int. Cl.
*G06T 7/11* (2017.01)
*G06T 7/149* (2017.01)
(Continued)

(52) U.S. Cl.
CPC .............. *G06T 7/11* (2017.01); *G06T 7/149* (2017.01); *G16H 50/20* (2018.01); *G16H 50/50* (2018.01);
(Continued)

(58) Field of Classification Search
None
See application file for complete search history.

(56) References Cited

U.S. PATENT DOCUMENTS

| 2008/0002870 A1* | 1/2008 | Farag | G06V 10/761 382/209 |
| 2019/0205606 A1* | 7/2019 | Zhou | G06F 18/285 |

(Continued)

OTHER PUBLICATIONS

D. G. Elliman and P. J. Connor, "Orientation and scale invariant symbol recognition using a hidden Markov model," 1992 International Conference on Image Processing and its Applications, Maastricht, Netherlands, 1992, pp. 331-334 (Year: 1992).*

(Continued)

*Primary Examiner* — Amandeep Saini
*Assistant Examiner* — Caroline Tabancay Duffy
(74) *Attorney, Agent, or Firm* — Dentons Bingham Greenebaum LLP; Brian W. Chellgren

(57) ABSTRACT

Assessment of pulmonary function in coronavirus patients includes use of a computer aided diagnostic (CAD) system to assess pulmonary function and risk of mortality in patients with coronavirus disease 2019 (COVID-19). The CAD system processes chest X-ray data from a patient, extracts imaging markers, and grades disease severity based at least in part on the extracted imaging markers, thereby distinguishing between higher risk and lower risk patients.

14 Claims, 16 Drawing Sheets

(51) Int. Cl.
*G16H 50/20* (2018.01)
*G16H 50/50* (2018.01)

(52) U.S. Cl.
CPC .............. *G06T 2207/10081* (2013.01); *G06T 2207/20081* (2013.01); *G06T 2207/20084* (2013.01); *G06T 2207/30061* (2013.01)

(56) References Cited

U.S. PATENT DOCUMENTS

2021/0304408 A1* 9/2021 Chaganti .................. G06T 7/11
2021/0319546 A1* 10/2021 Kang ..................... G06V 10/70

OTHER PUBLICATIONS

Soliman, A et al., "Accurate lungs segmentation on CT chest images by adaptive appearance-guided shape modeling," IEEE transactions on medical imaging, vol. 36, pp. 263-276, 2016.
Kundu, S., Elhalawani, H., Gichoya, J.W., and Kahn Jr, C.E., "How Might AI and Chest Imaging Help Unravel COVID-19's Mysteries?" 2020.
Wu, X. et al., "Deep learning-based multi-view fusion model for screening 2019 novel coronavirus pneumonia: a multicentre study," Eur. J. Radiol., 2020.
Fu, L. et al., "Clinical characteristics of coronavirus disease 2019 (covid-19) in china: a systematic review and meta-analysis," J. Infect., 2020.
Rodriguez-Morales, A.J. et al., "Clinical, laboratory and imaging features of covid-19: A systematic review and metaanalysis," Travel. Medicine Infectious Disease, 2020.
Quian, G.Q. et al, Epidemiologic and clinical characteristics of 91 hospitalized patients with COVID-19 in Zhejiang, China: a retrospective, multi-centre case series, QJM: An Int. J. Medicine, 2020.
Chen, J. etal., "Clinical progression of patients with covid-19 in shanghai, china," J. Infect., 2020.
Su, S. et al., "Epidemiology, genetic recombination, and pathogenesis of coronaviruses," Trends Microbiology, vol. 24, pp. 490-502, 2016.
Zhu, N. et al., "A novel coronavirus from patients with pneumonia in china, 2019," New Engl. J. Medicine, 2020.
Ai, T. et al., "Correlation of chest ct and rt-pcr testing in coronavirus disease 2019 (covid-19) in china: A report of 1014 cases," Radiology, 2020.
Xie, X. et al., "Chest ct for typical 2019-ncov pneumonia: relationship to negative rt-pcr testing," Radiology, 2020.
Auld, S. et al., "ICU and ventilator mortality among critically ill adults with covid-19," MedRxiv, 2020.
Lan, L. et al., "Postiive RT-PCR Test Results in Patients Recovered From COVID-19," JAMA, 2020.
Waller, J.V. et al, "Diagnostic tools for coronavirus disease (covid-19): Comparing ct and rt-pcr viral nucleic acid testing," Am. J. Roentgenol. 1-5, 2020.
Chen, D. et al., "Can chest ct features distinguish patients with negative from those with positive initial rt-pcr results for coronavirus disease (covid-19)?" Am. J. Roentgenol. 1-5, 2020.
Jacobi, A., Chung, M., Bernheim. A., and Eber, C., "Portable chest x-ray in coronavirus disease-19 (covid-19): A pictorial review," Clin. Imaging, vol. 64, pp. 35-42, 2020.
Wong, H.Y.F. et al., "Frequency and distribution of chest radiographic findings in covid-19 positive patients," Radiology, 2020.
Yoon, S.H. et al., "Chest radiographic and ct findings of the 2019 novel coronavirus disease (covid-19): analysis of nine patients treated in korea," Korean Journal Radiology, vol. 21, pp. 494-500, 2020.
Borhesi, A. and Maroldi, R., "Covid-19 outbreak in italy: experimental chest x-ray scoring system for quantifying and monitoring disease progression," La Radiol. Medica, 2020.
Schiaffino, S. et al., "Diagnostic performance of chest x-ray for covid-19 pneumonia during the sars-cov-2 pandemic in lombardy, italy," J. Thorac. Imaging, 2020.
Liu, F. et al., "Ct quantification of pneumonia lesions in early days predicts progression to severe illness in a cohort of covid-19 patients," Theranostics vol. 10, p. 5613, 2020.
Li, L. et al., "Artificial intelligence distinguishes covid-19 from community acquired pneumonia on chest ct.," Radiology, 2020.
Belfiore, M.P. et al., "Artificial intelligence to codify lung ct in covid-19 patients," La Radiologica Medica 1-5, 2020.
Ito, R., Iwano, S., and Naganawa, S., "A review on the use of artificial intelligence for medical imaging of the lungs of patients with coronavirus disease 2019," Diagn. Interv. Radiol., 2020.
Mei, X. et al., "Artificial intelligence-enabled rapid diagnosis of patients with covid-19," Nat. Medicine 1-5, 2020.
Bai, H.X. et al., "AI augmentation of radiologist performance in distinguishing covid-19 from pneumonia of other etiology on chest ct.," Radiology, 2020.
Li, D. et al., "False-negative results of real-time reverse-transcriptase polymerase chain reaction for severe acute respiratory syndrome coronavirus 2: role of deep-learning-based ct diagnosis and insights from two cases," Korean Journal Radiology, vol. 21, pp. 505-508, 2020.
Hurt, B., Kligerman, S. and Hsiao, A., "Deep learning localization of pneumonia: 2019 coronavirus (covid-19) outbreak," J. Thorac. Imaging, vol. 35, pp. W87-W89, 2020.
Narin, A., Kaya, C., and Pamuk, Z., "Automatic detection of coronavirus disease (covid-19) using x-ray images and deep convolutional neural networks," arXiv preprint arXiv:2003.10849, 2020.
Hassanien, A. E., Mahdy, L. N., Ezzat, K. A., Elmousalami, H. H., and Ella, H. A., "Automatic x-ray covid-19 lung image classification system based on multilevel thresholding and support vector machine, "MedRxi. 2020.
Apostolopoulos, I., Aznaouridis, S., and Tzani, M., "Extracting possibly representative covid-19 biomarkers from x-ray images with deep learning approach and image data related to pulmonary diseases," arXiv preprint arXiv:2004.00338, 2020.
Wang, L. and Wong, A., "Covid-net: A tailored deep convolutional neural network design for detection of covid-19 cases from chest radiography images," arXiv preprint arXiv:2003.09871, 2020.
Hammoudi, K. et al., "Deep learning on chest x-ray images to detect and evaluate pneumonia cases at the era of covid-19" arXiv preprint arXiv:2004.03399, 2020.
Iwanami, T., Goto, T., Hirano, S., and Sakurai, M., "An adaptive contrast enhancement using regional dynamic histogram equalization," IEEE International Conference on Consumer Electronics (ICCE), pp. 719-722, 2012.
Cohen, J. P., Morrison, P., and Dao, L., "Covid-19 image data collection," arXiv 2003.11597, 2020.
Zhou, F. et al., "Clinical course and risk factors for mortality of adult inpatients with covid-19 in wuhan, china: a retrospective cohort study," The lancet, 2020.
Iyengar, K., Bahl S., Vaishya, R., and Vaish, A., "Challenges and solutions in meeting up the urgent requirement of ventilators for covid-19 patients," Diabetes & Metab. Syndr. Clin. Res. & Rev., 2020.
Geier, M. R. and Geier, D. A., "Respiratory conditions in coronavirus disease 2019 (covid-19): Important considerations regarding novel treatment strategies to reduce mortality," Med. Hypotheses, 2020.
Mohlenkamp, S. and Thiele, H., "Ventilation of covid-19 patients in intensive care units," Herz, vol. 45, pp. 329-331, 2020.
Bhatraju, P. K. et al., "Covid-19 in critically ill patients in the seattle region—case series," New Engl. J. Medicine, vol. 382, pp. 2012-2022, 2020.
Arentz, M. et al., "Characteristics and outcomes of 21 critically ill patients with covid-19 in washington state," JAMA, vol. 323, pp. 1612-1614, 2020.
Intensive Care National Audit & Research Centre, "ICNARC report on COVID-19 in critical care," May 15, 2020.
Richardson, S. et al., "Presenting characteristics, comorbidities, and outcomes among 5700 patients hospitalized with covid-19 in the new york city area," JAMA, 2020.

(56) References Cited

OTHER PUBLICATIONS

Wu, C. et al., "Risk factors associated with acute respiratory distress syndrome and death in patients with coronavirus disease 2019 in wuhan, china," JAMA Internal Medicine, 2020.

* cited by examiner

ASSESSMENT OF PULMONARY FUNCTION IN CORONAVIRUS PATIENTS

CROSS-REFERENCE TO RELATED APPLICATION

This application claims the benefit of U.S. provisional patent application Ser. No. 63/156,171, filed Mar. 3, 2021, incorporated herein by reference.

FIELD OF THE INVENTION

Assessment of pulmonary function in coronavirus patients includes use of a computer aided diagnostic (CAD) system to assess pulmonary function and risk of mortality in patients with coronavirus disease 2019 (COVID-19). The CAD system processes chest X-ray data from a patient, extracts imaging markers, and grades disease severity based at least in part on the extracted imaging markers, thereby distinguishing between higher risk and lower risk patients.

BACKGROUND OF THE INVENTION

COVID-19 is caused by a novel RNA virus belonging to the Coronaviridae family. Coronaviridae is a family of nonsegmented, enveloped, positive-sense, single-stranded ribonucleic acid viruses. Six species of coronavirus had previously been identified as pathogenic in humans: four of these cause mild respiratory illnesses, whereas the other two species, severe acute respiratory syndrome coronavirus (SARS-CoV) and Middle East respiratory syndrome coronavirus (MERS-CoV), have led to epidemics with significant rates of mortality.

The clinical diagnosis of COVID-19 depends on different symptoms including fever (98% of cases), dry cough (75%), fatigue (45%), muscle aches (45%), difficulty breathing (55%), and acute respiratory distress syndrome (ARDS) (20%). Severe cases may progress to multiorgan dysfunction and even death (2.5%). The disease may be classified as (i) mild type: moderate clinical symptoms with normal chest X-ray; (ii) typical type: fever, respiratory, and other clinical findings indicating signs of pneumonia; (iii) severe type: respiratory distress signs (respiratory rate≥30 breaths per minute and/or blood oxygen saturation of less than 93%); or (iv) critical type: dysfunction of respiration necessitating mechanical ventilation, shock, and organ damage requiring monitoring and treatment from an intensive care unit (ICU).

Due to the wide variations in clinical presentation and progression rate for COVID-19, laboratory confirmation of SARSCoV-2 infection is essential to initiate appropriate early treatment and to prevent further spread of the disease. The current reference standard for this purpose is real-time reverse transcription polymerase chain reaction (PCR) of viral RNA. The PCR test, according to current guidelines, is run on samples from nasopharyngeal and/or throat swabs. While PCR is the gold standard in diagnosing patients with COVID-19 infection, the sensitivity of a single PCR is suboptimal and depends on the timing of the test, sampling sites and sampling techniques.

Chest radiography is helpful for first-line evaluation of patients with a high pre-test probability of overt COVID-19 pneumonia, clinical follow up, and for the evaluation of potential complications. Chest radiography can detect areas of ground glass density, also observed on chest computed tomography (CT), which may often have a correlation with the severity of the disease, and may be intermixed with reticular pattern.

Based on recent clinical research, COVID-19 radiological forms are variable in severity using plain radiography or CT, ranging from a normal chest (albeit rarely), to patchy involvement of one or both lungs in mild or moderate cases, to diffuse infiltration (white lung) in severe cases. This is an important issue, as mild or moderate cases can be managed by medical treatment or non-invasive ventilation, while severe cases with bilateral lung infection urgently need mechanical ventilation to support respiration as patients develop ARDS. Given the paucity of mechanical ventilation units, patient selection for ventilation plays a crucial role in saving lives.

There are few preliminary studies and case reports discussing the role of artificial intelligence (AI) on plain radiography and CT for early diagnosis of patients with COVID-19. AI can be used in conjunction with radiologists to improve the results of detection of COVID-19. AI can be a powerful aid in delineating and quantifying lesions in X-ray images and in tracking longitudinal changes between exams, which is crucial for precision medicine. In essence, AI is another means of analyzing data that clinicians can draw on to inform their judgment in issues of triage, diagnosis (in combination with PCR tests and epidemiological risk), prognosis, and selection between therapeutic alternatives in patients exhibiting COVID-19 symptoms. Plain radiography involves a low radiation dose compared to CT and is better suited for routine monitoring and follow up as compared to a CT scan. AI may be capable of detecting subtle changes in the lung visible on either chest X-ray or CT, and can improve efficiency by decreasing the amount of time to return test results. This is necessary for screening the general population during the current COVID-19 pandemic and in the epicenters of any future outbreaks. Computer assisted detection alleviates the burden on radiologists and clinicians and facilitates rapid triage. Also, AI can be used for the differentiation of previous lung injury unrelated to COVID-19 from advanced lung dysfunction due to COVID-19, and assist in patient selection for ventilation. However, CAD systems for assessing lung function in COVID-19 are limited in the literature.

X-ray images may be indicative of healthy lungs or evidence of pneumonia (bacterial or viral). Combined with prior information regarding the likelihood the patient has been exposed to the virus, an automatic diagnosis of viral pneumonia has a high true positive rate for detection of COVID-19. Currently, the primary challenge is to apply different AI-based approaches to determine the severity of chest infection in COVID-19 patients given that X-ray images vary enormously in image quality due to the wide range of X-ray machines in use across the world.

SUMMARY

To address the identified challenges, Applicant has developed a novel CAD system using AI and machine learning techniques to assist physicians by providing an objective metric that can differentiate severe cases of COVID-19 from mild/moderate non-severe cases. The CAD system addresses the challenge of X-ray image quality by generating a diagnosis at least in part on extracted X-ray image markers that are invariant under rotation, scaling, and translation, and that capture both local and global features of the lung.

It will be appreciated that the various systems and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

A better understanding of the present invention will be had upon reference to the following description in conjunction with the accompanying drawings.

DETAILED DESCRIPTION OF THE PREFERRED EMBODIMENTS

Figure 1:
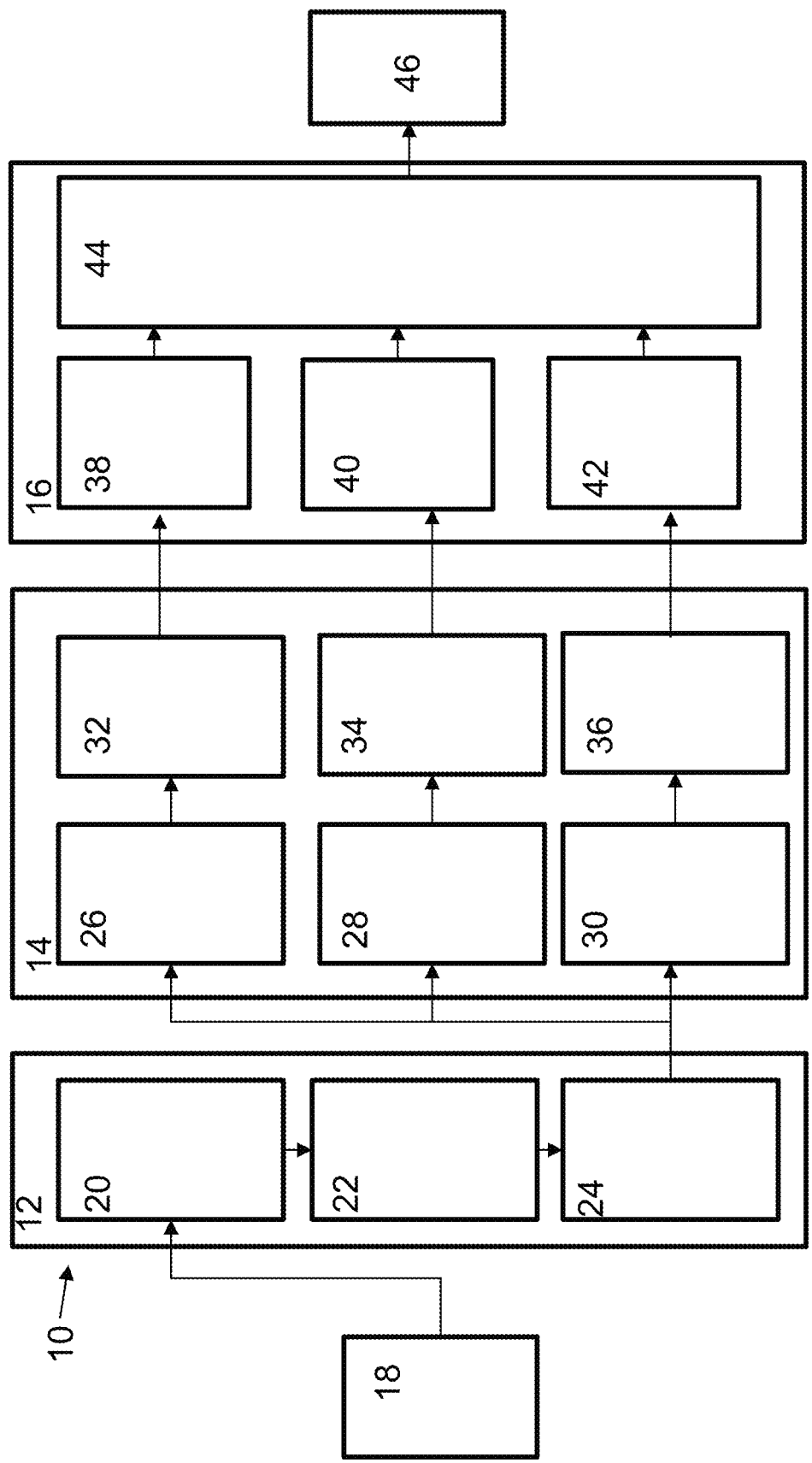
FIG. 1 is a diagram representing the methodology of the disclosed CAD system for assessment of pulmonary function.
Figure 2A:
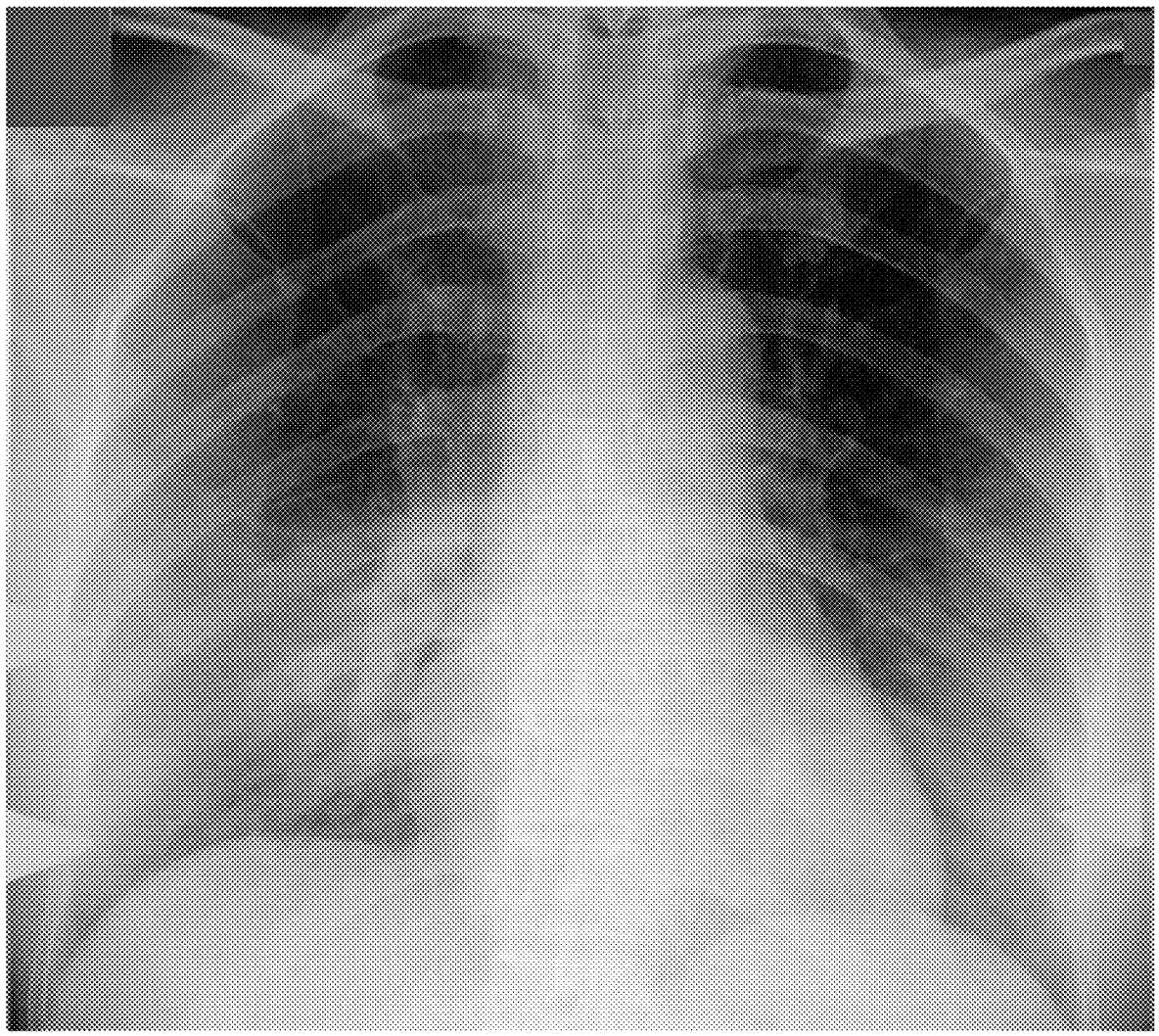
FIG. 2A is an original pulmonary X-ray image

FIG. 1 illustrates an exemplary CAD system for assessment of pulmonary function in patients with Coronaviridae infection and the method for assessing pulmonary function performed thereby. The method 10 broadly includes three sections: (i) preprocessing steps 12 to improve contrast of medical image data, such as an X-ray image, that includes image data of at least one lung and to identify the region of interest in order to enhance diagnostic accuracy of subsequent steps; (ii) modeling steps 14 model the appearance of infected unhealthy chest tissue using a new Markov-Gibbs random field (MGRF) constructed to be invariant under rotation, translation, and change of scale; and (iii) determining steps 16 performed by a neural network (NN)-based fusion and diagnostic system to determine whether the severity of lung infection is at a first state, e.g., non-severe or low severity, or a second state, e.g., severe or high severity. In other embodiments, the NN-based fusion and diagnostic system may determine whether the severity of lung infection is one of a plurality of states, e.g., mild, moderate, or severe. The CAD system receives as input for the method 10 medial image data 18, such as a thoracic X-ray image of a subject patient (FIG. 2A), which includes image data of the lung region.

Data Preprocessing

Figure 2B:
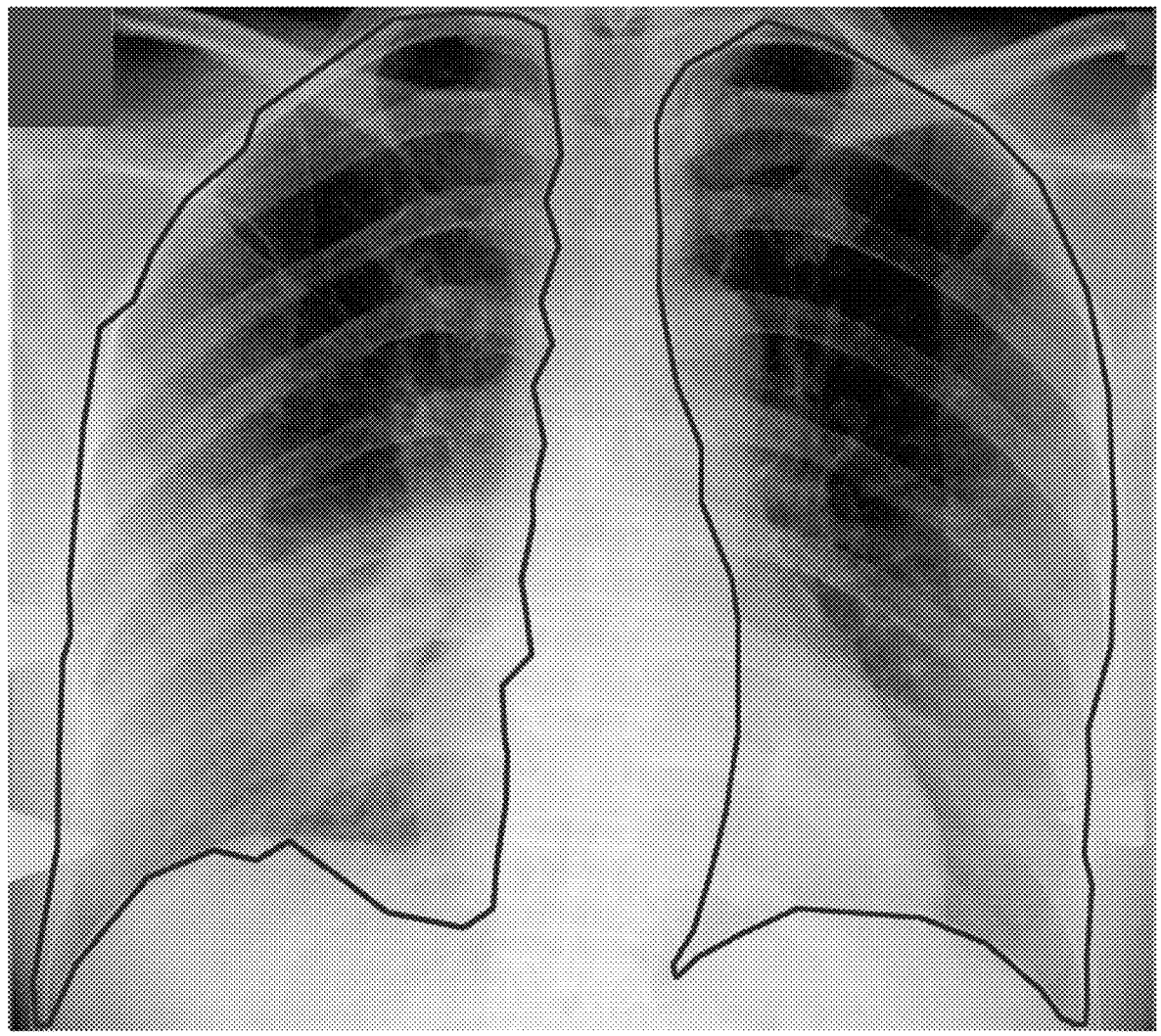
FIG. 2B is the image of FIG. 2A including a roughly segmented lung region.
Figure 2C:
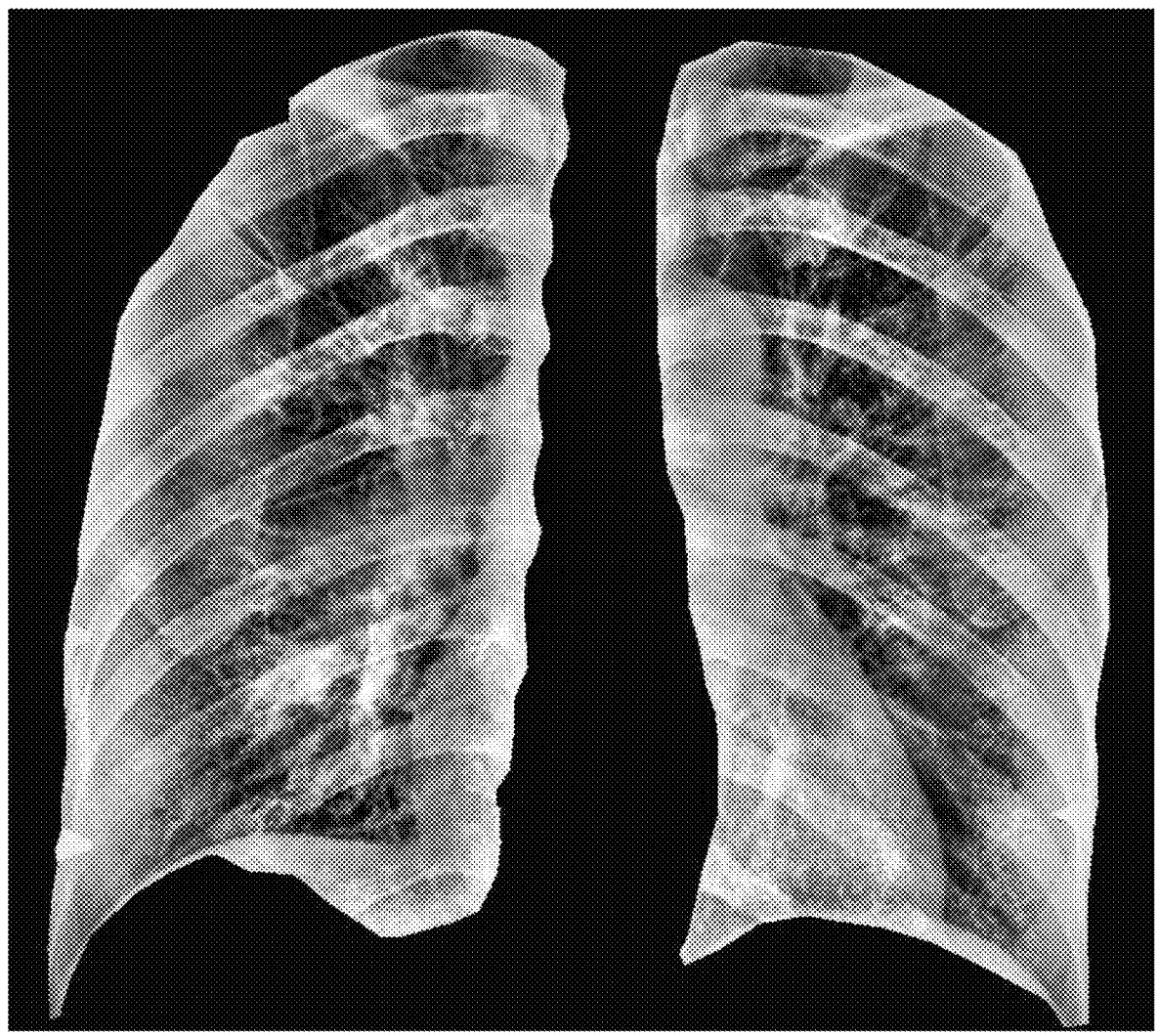
FIG. 2C is the image of FIG. 2B with enhanced contrast of the lung region.

In this exemplary embodiment, the preprocessing steps 12 include three sequential steps to improve the accuracy of the methodology. In the first preprocessing step 20, the medical image is segmented to identify the lung region (FIG. 2B). This may be performed manually using computer-based methods as described in Soliman, A., Khalifa, F., Elnakib, A., Abou El-Ghar, M., Dunlap, N., Wang, B., Gimel'farb, G., Keynton, R. and El-Baz, A., 2016. *Accurate lungs segmentation on CT chest images by adaptive appearance-guided shape modeling*. IEEE transactions on medical imaging, 36(1), pp. 263-276, incorporated herein by reference, or other computer-based methods. In the second preprocessing step 22, regional dynamic histogram equalization (RDHE) is utilized to reduce the effect of certain kinds of noise and enhance lung tissue contrast. This approach divides the image into blocks x rows high by y columns wide. Then, dynamic histogram equalization is applied within each block to adaptively enhance the contrast. Therefore, the image histogram is remapped by block, and pixel values are adjusted relative to the other pixels in their x×y neighborhood. The contrast-enhanced X-ray image resulting from the RDHE approach is illustrated in FIG. 2C.

Figure 2D:
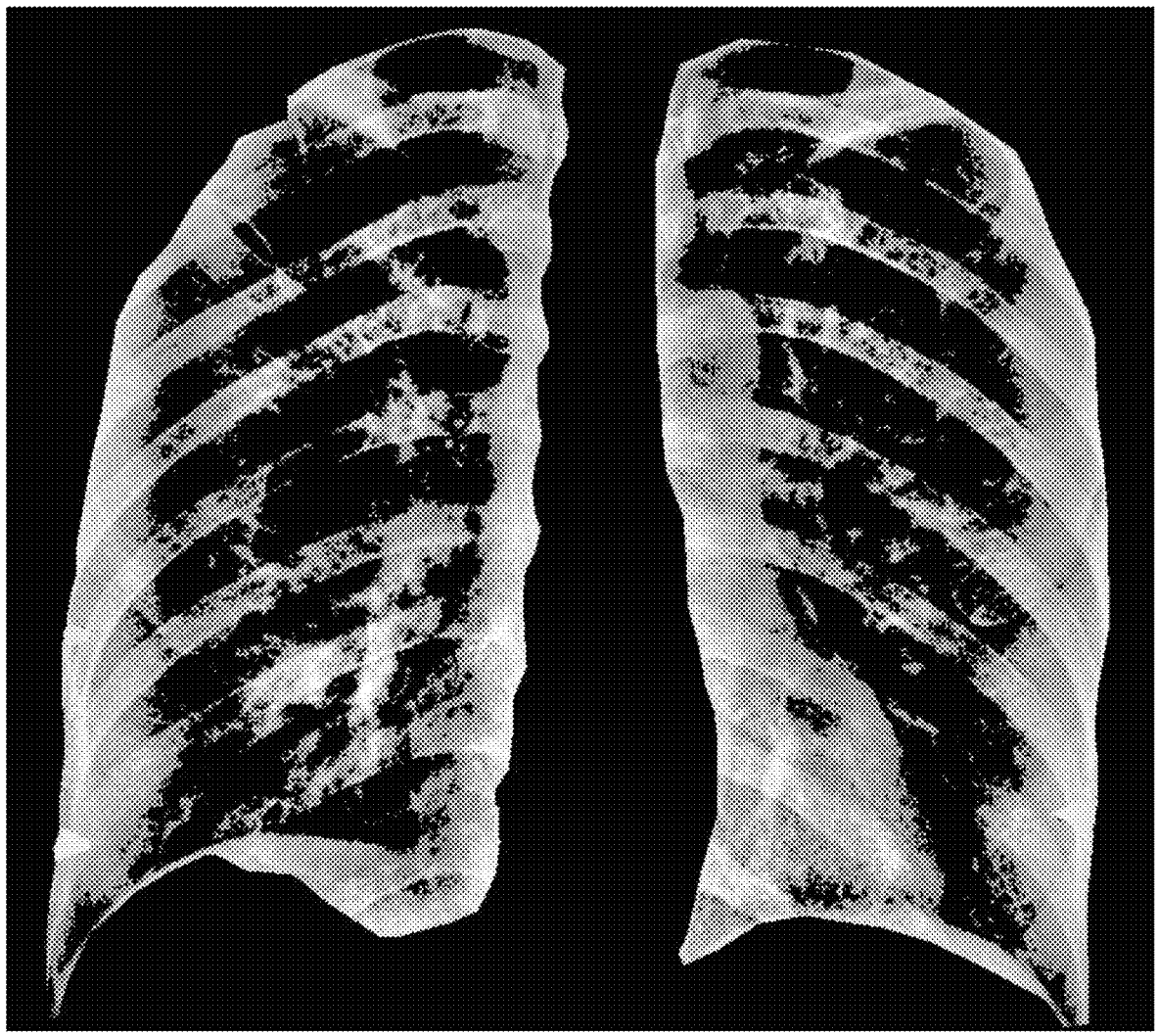
FIG. 2D is the image of FIG. 2C with extracted candidate abnormal tissues.

The third preprocessing step 24 is to identify and mask off the healthy lung tissues from the infected tissues. This step narrows the search space to focus only on the abnormal tissues and serves to increase the diagnostic accuracy of the CAD system. This third step is elaborated in El-Baz, A., Gimel'farb, G. & Suri, J. *Stochastic Modeling for Medical Image Analysis* (Boca Raton: CRC Press, 2016), incorporated herein by reference, and considers both the spatial interaction between nearby image pixels and the intensity distribution of those pixels within the lung region of interest. The instant invention follows the conventional description of the MGRF model in terms of independent signals (images) and interdependent region labels (segmentations) as described in the published article, but focuses on more accurate model identification. Each image segment corresponds to a single dominant mode of the empirical distribution (i.e. histogram) of gray levels. To identify the dominant modes, each image histogram is considered to be sampled from a linear combination of discrete Gaussians (LCDG) distribution. An initial LCDG model is fit to the empirical distribution using a modified expectation-maximization (EM) algorithm. Free parameters of the LCDG to be optimized are the number of discrete Gaussian components and their respective weights (positive and negative), shape, and scale parameters. Then, the initial LCDG-based segmentation is iteratively refined using the MGRF model with its analytically estimated potentials. FIG. 2D displays the extracted pathological tissues using the algorithm disclosed herein.

Rotating, Scale, and Translation Invariant MGRF Model

Figure 3:
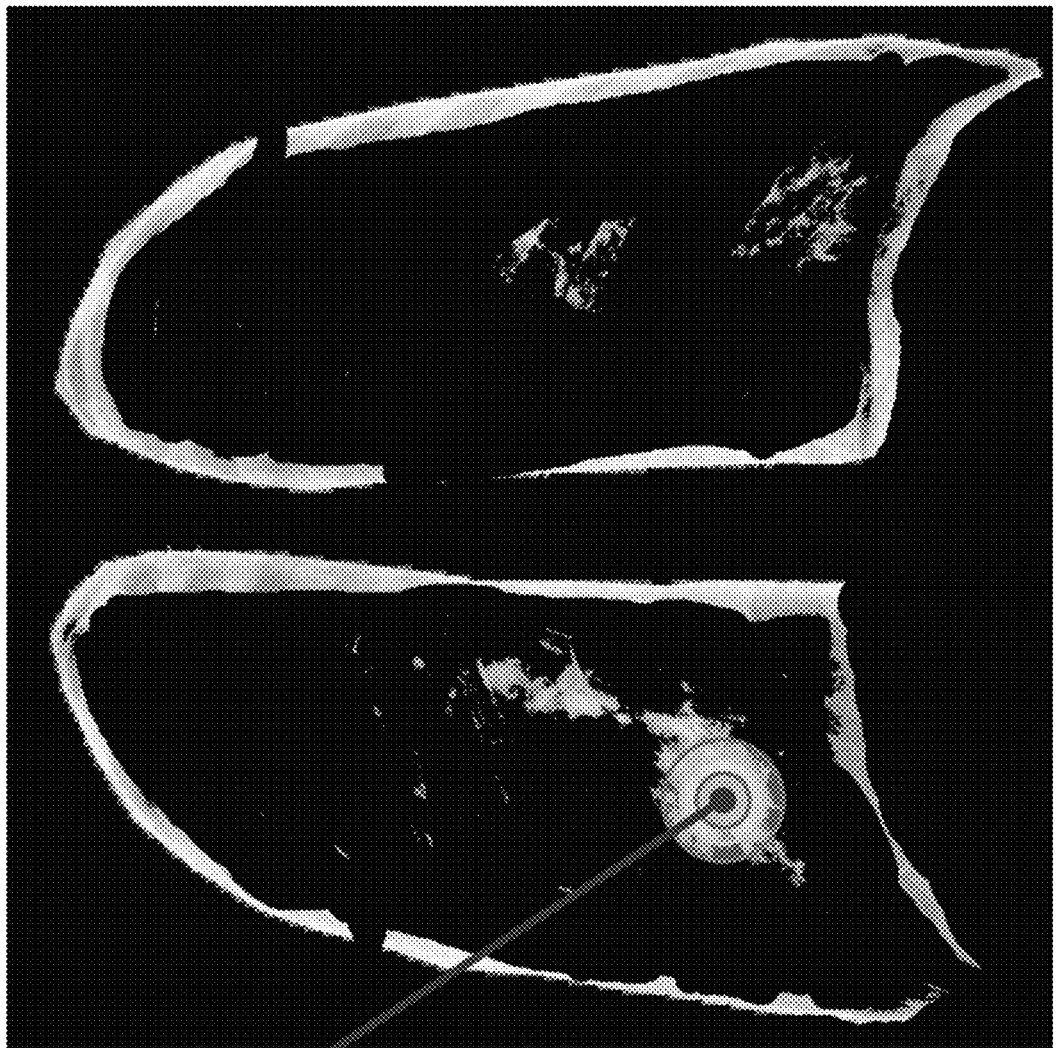
FIG. 3 is an illustration of rotation and translation invariant central-symmetric neighborhood sets for three different radii, $v_1$, $v_2$, and $v_3$ as obtained from chest X-ray image data.
Figure 4A:
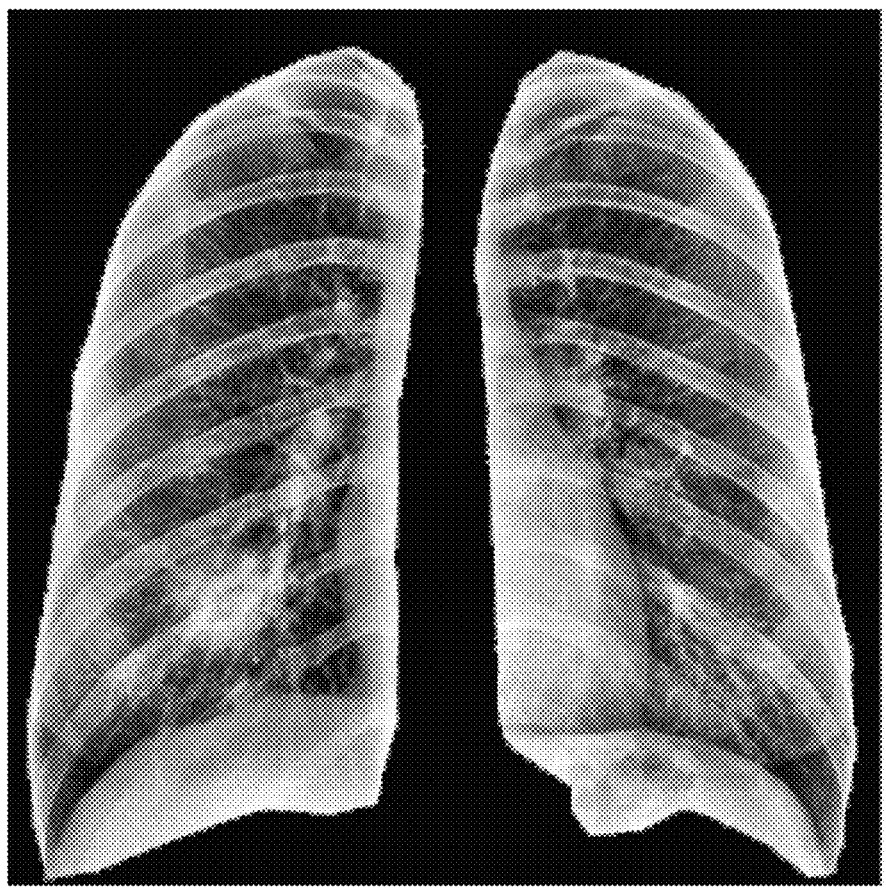
FIG. 4A displays chest X-ray images of a high severity case (upper panel) and a low severity case (lower panel).
Figure 4A:
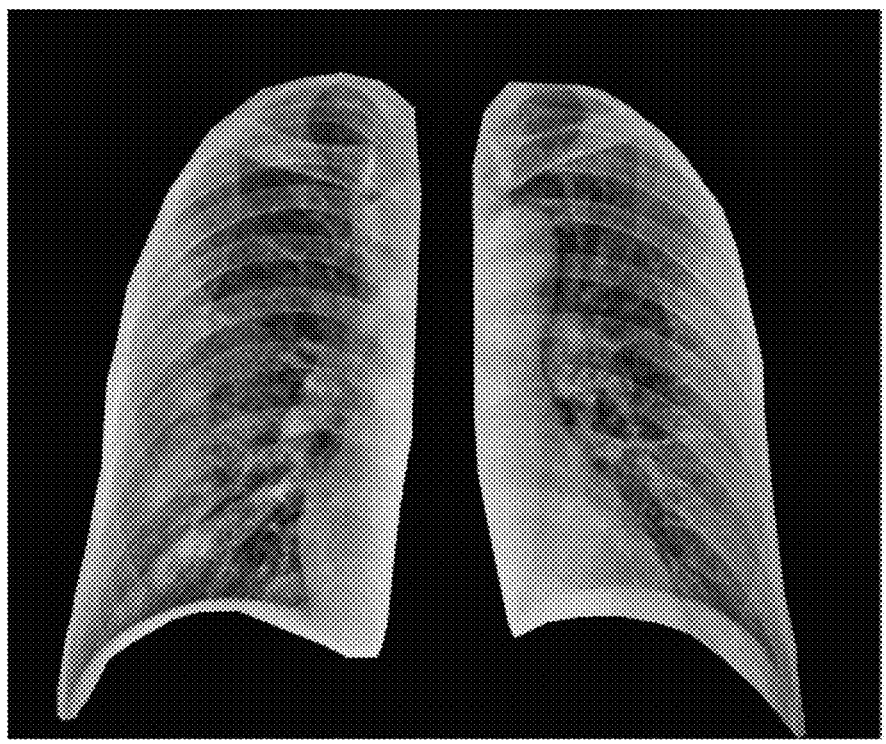
Figure 4B:
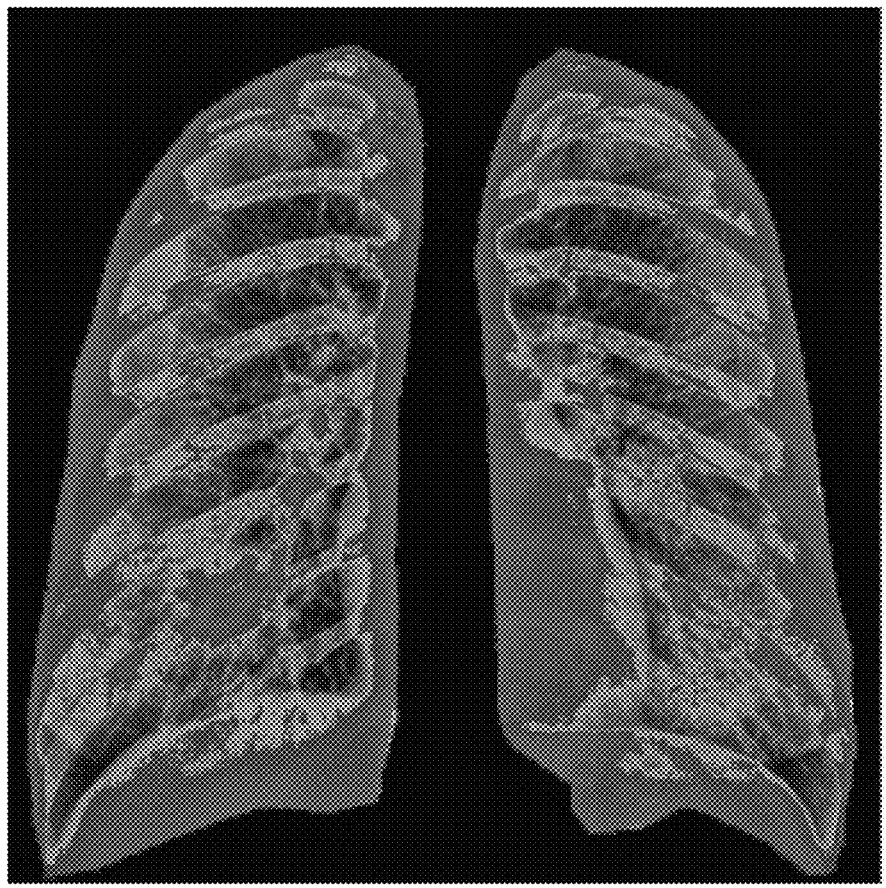
FIG. 4B displays the chest X-rays images of FIG. 4A, with estimated Gibbs energy at $v_1$ indicated by shading.
Figure 4B:
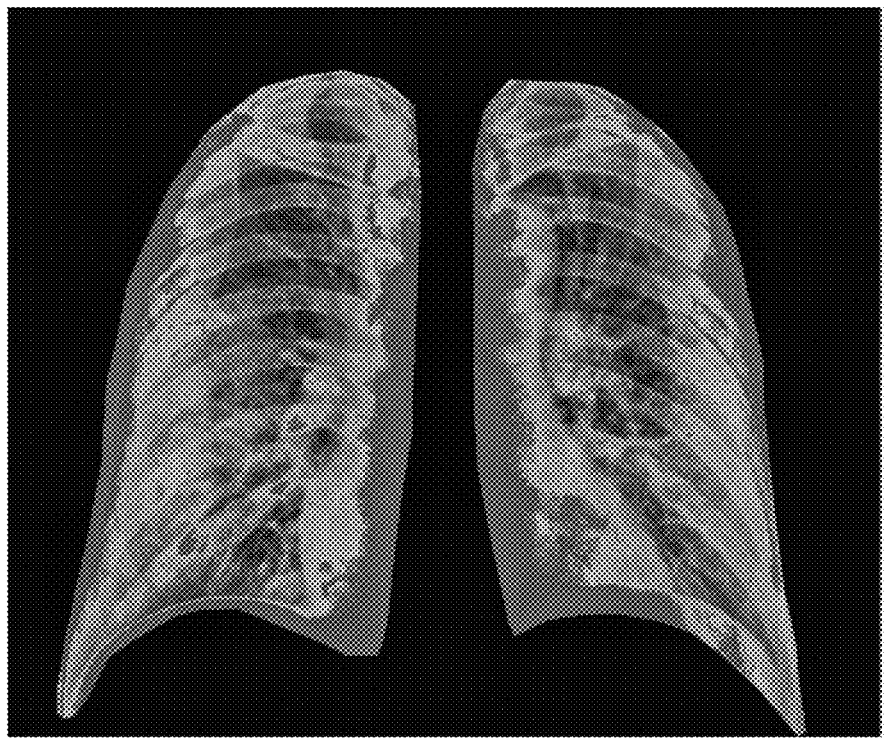
Figure 4C:
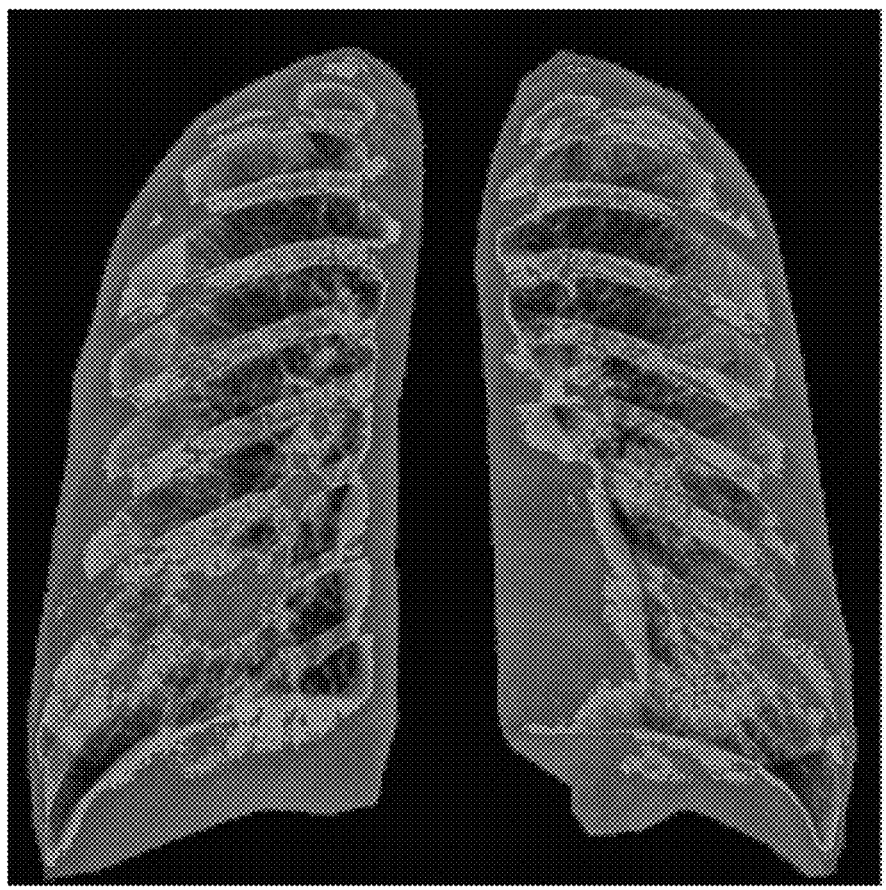
FIG. 4C displays the chest X-rays images of FIG. 4A, with estimated Gibbs energy at $v_2$ indicated by shading.
Figure 4C:
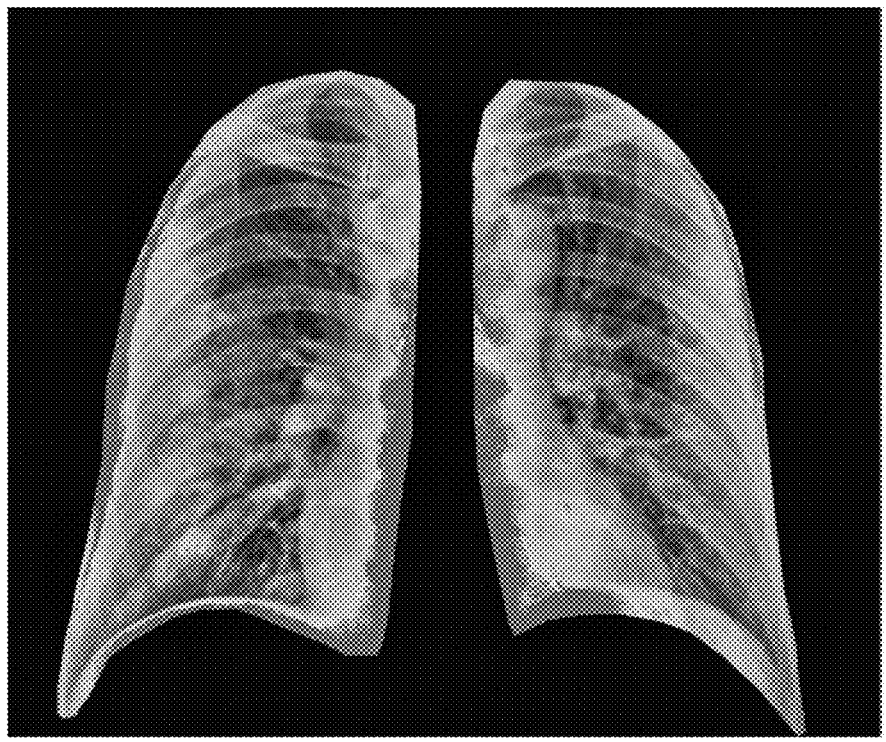
Figure 4D:
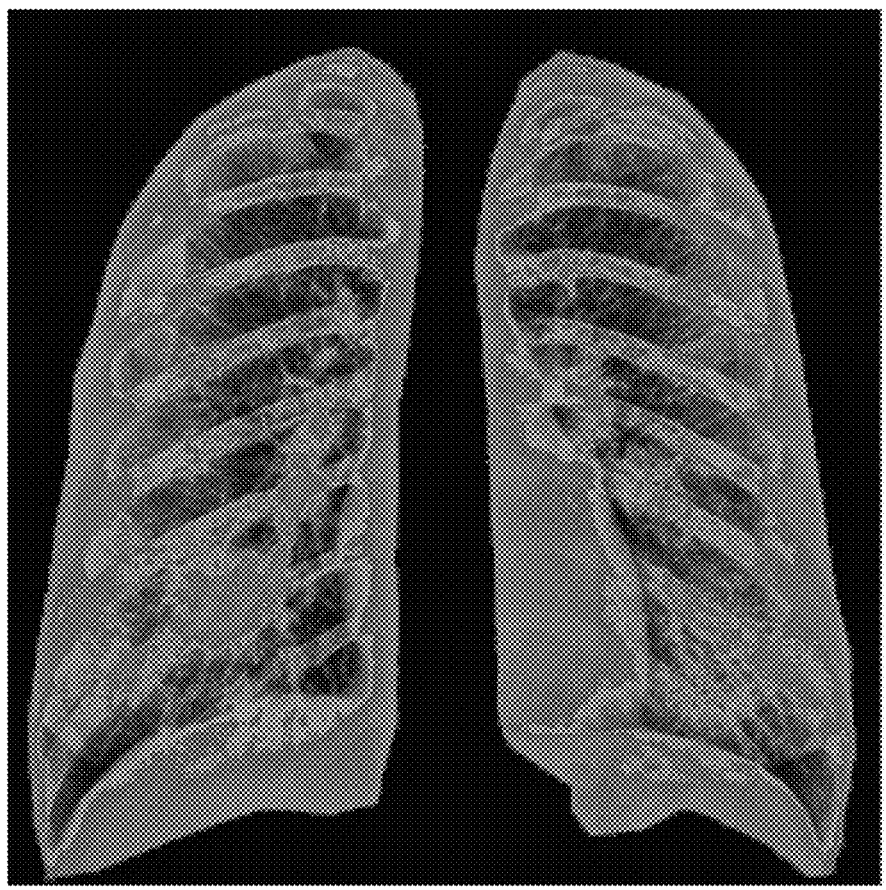
FIG. 4D displays the chest X-rays images of FIG. 4A, with estimated Gibbs energy at $v_3$ indicated by shading.
Figure 4D:
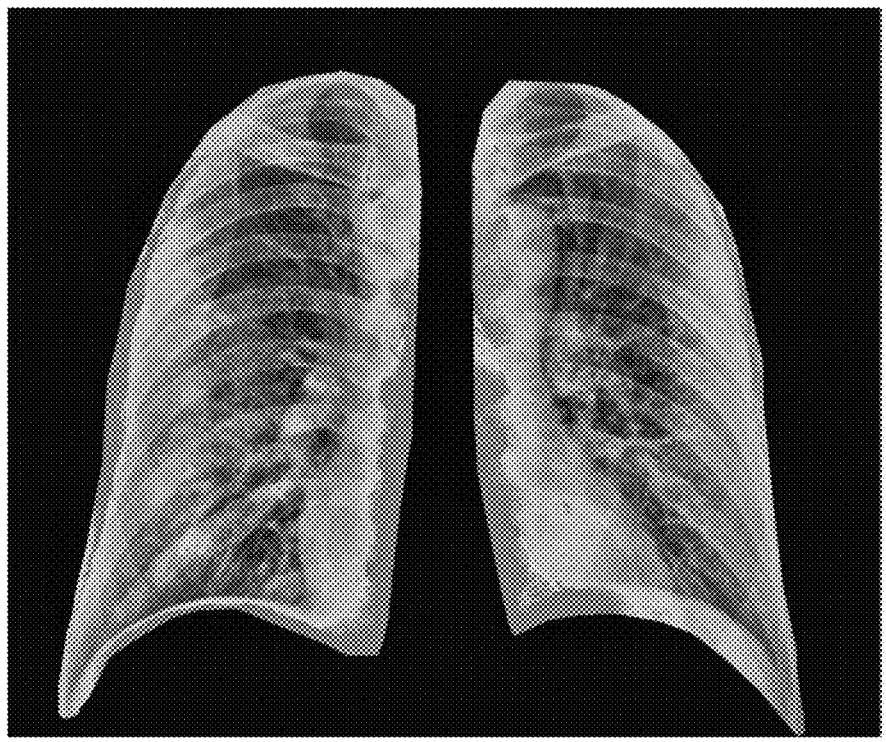

Moving on to the modeling steps 14, the proposed MGRF model was constructed such that that the medical image need not be aligned with any particular frame of reference in order to use it to grade the severity of lung infection as first state, e.g., non-severe or low severity, or second state, e.g., severe or high severity. To construct the appearance of the infected lung regions, the X-ray images are considered as samples from a piecewise stationary MGRF with a central-symmetric system of pixel-pixel interactions. Let $n_v$ denote a set of central-symmetric pixel neighborhoods indexed by $v \in \{1, \ldots, N\}$. Each $n_v$ is a set of coordinate offsets $(\xi, \eta)$ specified by a semi-open interval of interpixel distances $(d_{v,min}, d_{v,max})$ such that the $n_v$-neighborhood of pixel (x,y) comprises all pixels (x',y') such that $d_{v,min} \leq \sqrt{(x-x')^2 + (y-y')^2} \leq d_{v,max}$. A neighborhood system corresponding to $d_{v,min} = v - \frac{1}{2}$ and $d_{v,max} = v + \frac{1}{2}$, $v \in \{1,2,3\}$, is illustrated in FIG. 3. Associated with the neighborhood system is a set of N+1 Gibbs potential functions of gray value and gray value co-occurrences $V_0$: $Q \to \mathbb{R}$ and $V_v$: $Q \times Q \to \mathbb{R}$, $v \in \{1, \ldots, N\}$, where Q is the range of pixel gray levels, e.g. $Q = \{0, \ldots, 255\}$ in the case of 8-bit images.

For a given image/label map pair $(g_t, m_t)$ from the training set S, $t \in \{1, \ldots, T\}$, let $R_t = \{(x,y) | m_t(x,y) = ob\}$ denote the subset of the pixel lattice supporting the infected lung region. Denote the set of $n_v$-neighboring pixels restricted to $R_t$ by $$C_{v,t} = \{(x,y,x',y') | (x,y) \in R_t \wedge (x',y') \in R_t \wedge (x-x', y-y') \in n_v\}.$$

Finally, let $f_{0,t}$ and $f_{v,t}$, $v \in \{1, \ldots, N\}$ denote empirical probability distributions (i.e., relative frequency histograms) of gray values and gray value co-occurrences in the training infected region from the X-ray image $g_t$, $$f_{0,t}(q) = |R_t|^{-1} |\{(x,y) \in R_t | g_t(x,y) = q\}|; \qquad (1)$$

$$f_{v,t}(q,q') = |C_{v,t}|^{-1} |\{(x,y,x',y') \in C_{v,t} | g_t(x,y) = q \wedge g_t(x',y') = q'\}|. \qquad (2)$$

The joint probability of object pixels in image $g_t$ according to the MGRF model is given by the Gibbs distribution $$P_t = Z_t^{-1} \exp\left(\sum_{(x,y) \in R_t}\left(V_0(g_t(x,y)) + \sum_{v=1}^{N} \sum_{(\xi,\eta) \in n_v} V_v(g_t(x,y), g_t(x+\xi, y+\eta))\right)\right) \qquad (3)$$

$$= Z_t^{-1} \exp\left(|R_t|\left(V_{0,t}^T F_{0,t} + \sum_{v=1}^{N} \rho_{v,t} V_{v,t}^T F_{v,t}\right)\right),$$

where $\rho_{v,t} = |C_{v,t}|/|R_t|$ is an average cardinality of $n_v$ over the sublattice $R_t$.

Assuming lungs having the same pathology exhibit similar morphology in X-ray images, the previous expressions are approximated by their averages over the training set S: $|R_t| \approx R_{ob}$ and $|C_{v,t}| \approx C_{v,ob}$. Here $$R_{ob} = \frac{1}{T} \sum_{t=1}^{T} |R_t| \text{ and } C_{v,ob} = \frac{1}{T} \sum_{t=1}^{T} |C_{v,t}|.$$

Under the assumption that the observations in S are statistically independent (e.g., each X-ray is taken from a different patient), the expression for joint probability of object pixels may be likewise simplified:

$$P_S = \frac{1}{Z} \exp\left(TR_{ob}\left(V_0^T F_0 + \sum_{v=1}^{N} \rho_v V_v^T F_v\right)\right).$$

Here, $\rho_v = C_{v,ob}/R_{ob}$, and the probability vectors $F_{pix,ob}$ and $F_{v,ob}$ are the averages of the relative frequency histograms and normalized gray level co-occurrence matrices, respectively, over all objects in the training set. The problem of zero empirical probabilities, which can arise when a relatively small volume of the training data is available to identify the MGRF model, is dealt with using pseudocounts. Then Equations 1 and 2 are modified as follows:

$$f_{0,t}(q) = \frac{|\{(x,y) \in R_t | g_t(x,y) = q\}| + \varepsilon}{|R_t| + Q\varepsilon} \qquad (4)$$

$$f_{v,t}(q,q') = \frac{|\{(x,y,x',y') \in C_{v,t} | g_t(x,y) = q \wedge g_t(x',y') = q'\}| + \varepsilon}{|C_{v,t}| + Q^2\varepsilon}. \qquad (5)$$

The Bayesian quadratic loss estimate suggests using the offset $\varepsilon = 1$, while a more conservative approach suggests using $\varepsilon = 1/Q$ in Equation 4 and $\varepsilon = 1/Q^2$ in Equation 5.

Using the same analytical approach as in Gimel'farb, G. L. Image Textures and Gibbs Random Fields (Springer Netherlands, 1999), the Gibbs potential functions are approximated using the centered, training-set average, normalized histograms and co-occurrence matrices:

$$V_0(q) = \left(f_0(q) - \frac{1}{Q}\right); \qquad (6)$$

$$V_v(q,q') = \left(f_v(q,q') - \frac{1}{Q^2}\right).$$

Using the above estimated potentials, we can calculate the Gibbs energy of the infected lung region b in an X-ray image g as follows:

$$E(g,b) = V_0^T F_0(g,b) + \sum_{v \in N'} V_v^T F_v(g,b). \qquad (7)$$

Here, N' is a selected top-rank index subset of the neighborhoods, and the empirical probability distributions $F_0$ and $F_v$ are calculated over the object pixels b of g.

To summarize, the training approach is as follows: (1) read all infected regions from the training data having class "severe" lung infection; (2) calculate the co-occurrence of the image signal at a plurality of different radii (in this embodiment, $v_1$, $v_2$, and $v_3$); (3) normalize the co-occurrence frequency ($f_{pix,ob}(q)$); (4) estimate the Gibbs potential ($V_{pix,ob}(q)$) by using Equation 6 for each radii; (5) use Equation 7 to calculate the Gibbs energy (E(g,b)) for the training subjects. Gibbs energy calculated according to Equation 7 is a statistical estimator, i.e., a function of the observed data. In FIG. 1, boxes 26, 28, and 30 represent the calculated Gibbs energy at $v_1$, $v_2$, and $v_3$, respectively. CDF is used as a new scale-invariant representation of the estimated Gibbs energy, as explained below. In FIG. 1, box 32 represents the CDF for $v_1$, box 34 represents the CDF for $v_2$, and box 36 represents the CDF for $v_3$. Designating neighborhood sets and calculating Gibbs energy for a plurality of different radii allow for capture of both local features (using smaller radii) and global features (using larger radii) of lung lesions in the disclosed CAD system for assessment of pulmonary function for patients with infections, such as Coronaviridae infections, and more specifically, COVID-19.

NN-Based Fusion and Diagnostic System

Classification steps 16 are performed by artificial intelligence. Disclosed herein is an embodiment of a NN system that can fuse the diagnostic results from the three estimated Gibbs energy at three different radii. In other embodiments, two, four, five, or more different radii may be used. The NN system conceptually includes four blocks 38, 40, 42, and 44, each representing a neural network, as illustrated in FIG. 1. Three neural networks 38, 40, 42 are fed with the three different CDFs 32, 34, 36 of the estimated Gibbs energy at each radii as input, then the output of the three neural networks 38, 40, 42 are input into a fourth neural network 44, referred to here as a fusion neural network, and fused to generate a computer aided diagnosis 46 based on the input medical image data. In this exemplary embodiment, the diagnosis 46 may be classification as a first state, e.g., a low severity infection, or a second state, e.g., a high severity infection. In some embodiments, a backpropagation approach is used to train the NN-based diagnostic system as follows: (1) randomly initialize the weights of the proposed NN-network; (2) compute the output of each neuron in the hidden and output layers; (3) update the weights of the proposed NN-network using the batch-mode backpropagation approach; and (4) repeat steps 2 and 3 until there are no significant changes in the NN-network weights.

A hyper-parameters estimation approach is used to tune the hyper-parameters used in the NN system. The parameters to be estimated are the number of bins used to calculate CDF, the number of hidden layers in the NN model, the number of neurons in the hidden layer, and the activation function used to calculate the output of each neuron. Several experiments were run using random values for these parameters to estimate their optimal values using training data. All the results that are demonstrated in the following "Experimental Results" section have been obtained using the following setting: to handle all energy values, the chosen value for the number of CDF bins is 175; the number of hidden layers in the first neural network 38, second neural network 40, and fusion neural network 44 is one, while for the third neural network 42, there are no hidden layers (searching from 0 to 10); the number of neurons per hidden layer is 50, 20, and 2 for the first, second and fusion neural networks 38, 40, 44, respectively (searching from 1 to 200); and the sigmoid activation function has been selected after also considering the tangent and softmax activation functions. A neural network including one hidden layer is the generalized case prior to tuning hyper-parameters. However, in the particular case of tuning the hyper-parameters with respect to training data of COVID-19 positive patients, as described herein, no hidden layer was found to be necessary for the third neural network 42. In other embodiments, each neural network may include zero, one, or more than one hidden layers.

Experimental Results

To test and validate the system, data from a publicly available archive of COVID-19 positive cases, data from COVID-19 Open Research Dataset Challenge (CORD-19), and data from the University of Louisville, USA and Mansoura University, Egypt were used. These databases include 200 subjects tested as COVID-19 positive, 100 from patients who eventually died from the infection and 100 from patients who ultimately recovered. These databases comprise a heterogeneous collection of digital X-ray images, which was used to develop rotation, scale, and translation invariant MGRF model from which the imaging markers are extracted to grade the severity of lung infection in COVID-19 patients.

Figure 5A:
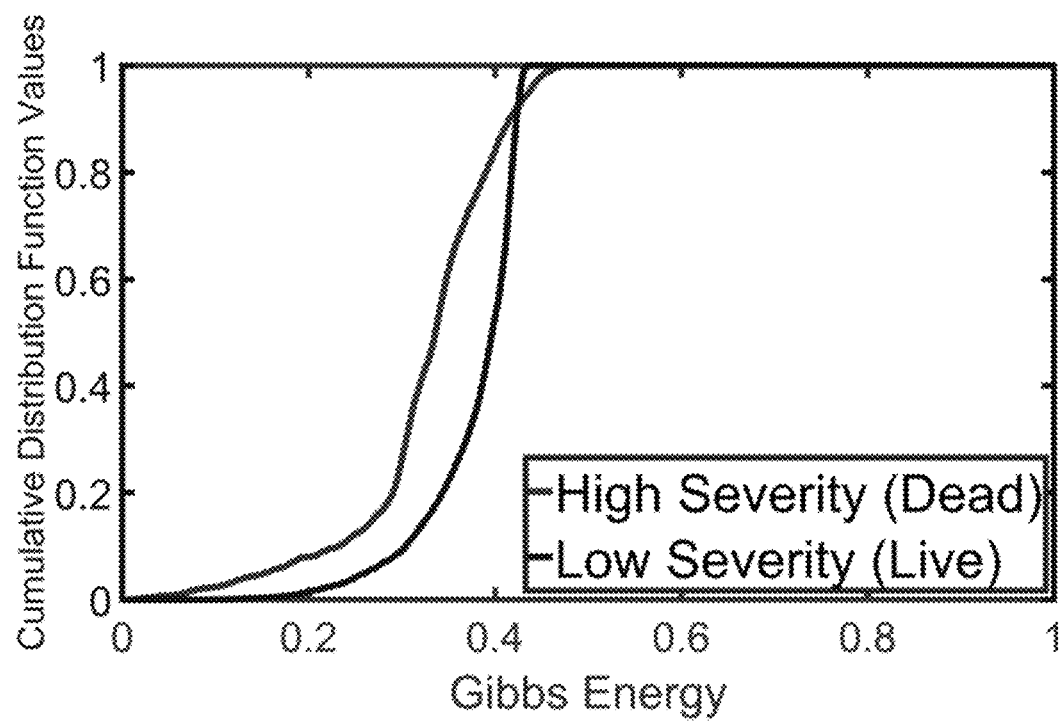
FIG. 5A is a graph comparing cumulative distribution function (CDF) values over Gibbs energy at radius $v_1$ for a subject with a high severity lung infection and a subject with a low severity lung infection.
Figure 5B:
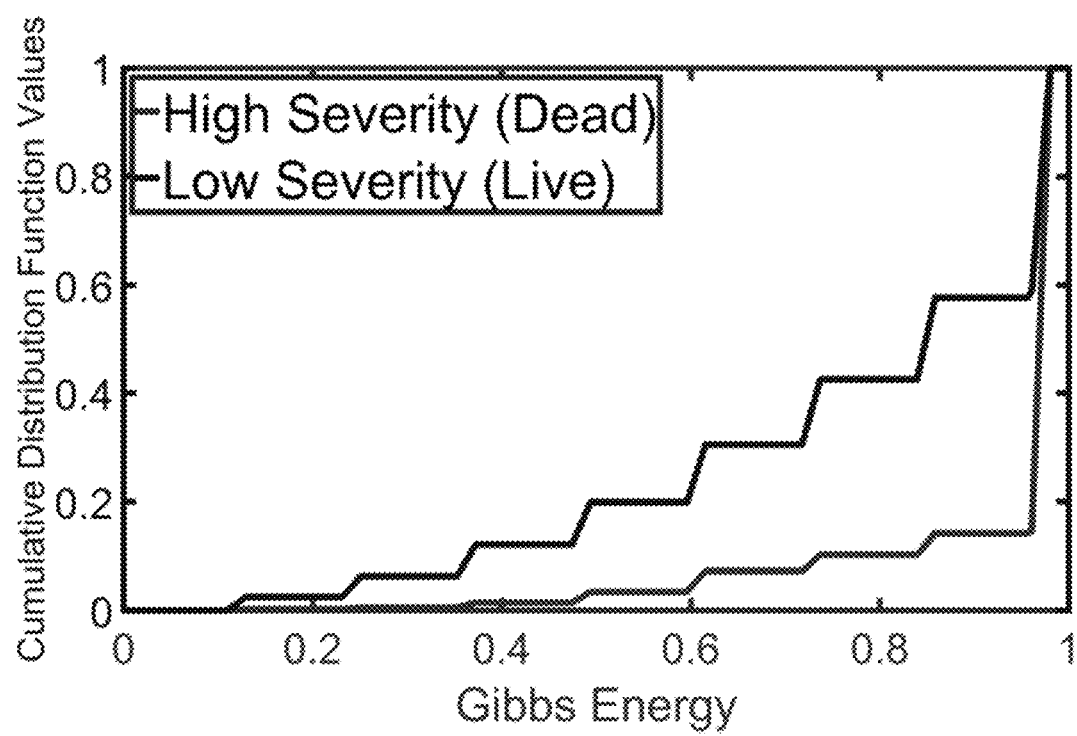
FIG. 5B is a graph comparing CDF values over Gibbs energy at radius $v_2$ for the subject with a high severity lung infection and the subject with a low severity lung infection of FIG. 5A.
Figure 5C:
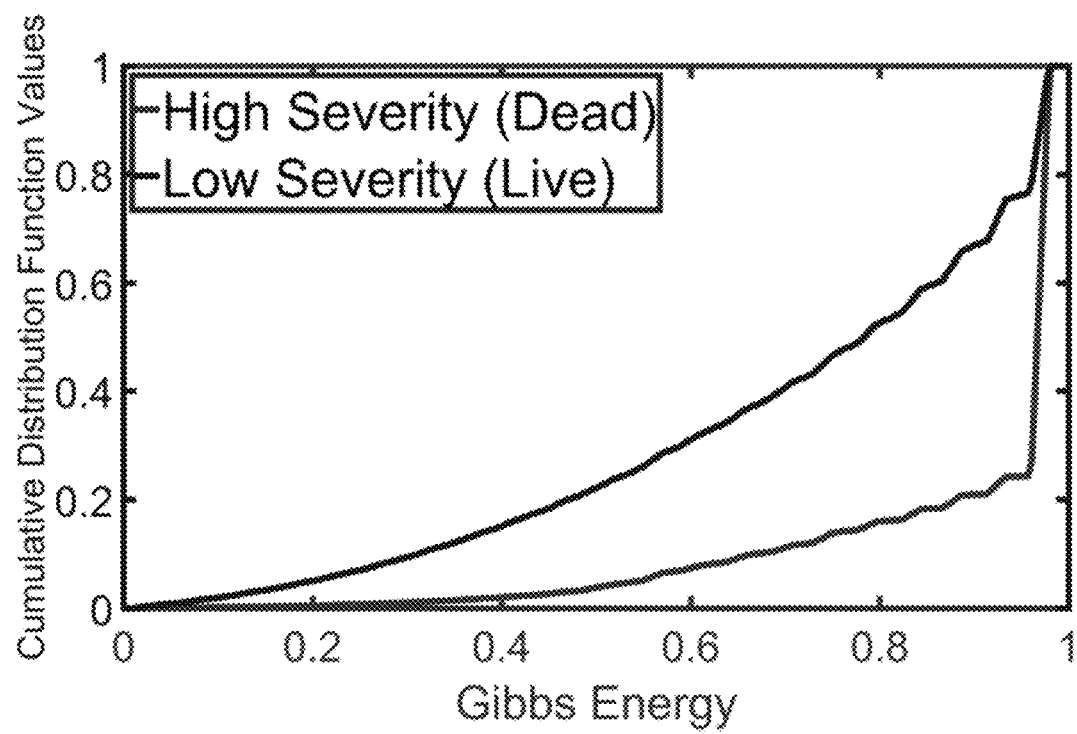
FIG. 5C is a graph comparing CDF values over Gibbs energy at radius $v_3$ for the subject with a high severity lung infection and the subject with a low severity lung infection of FIG. 5A.
Figure 6A:
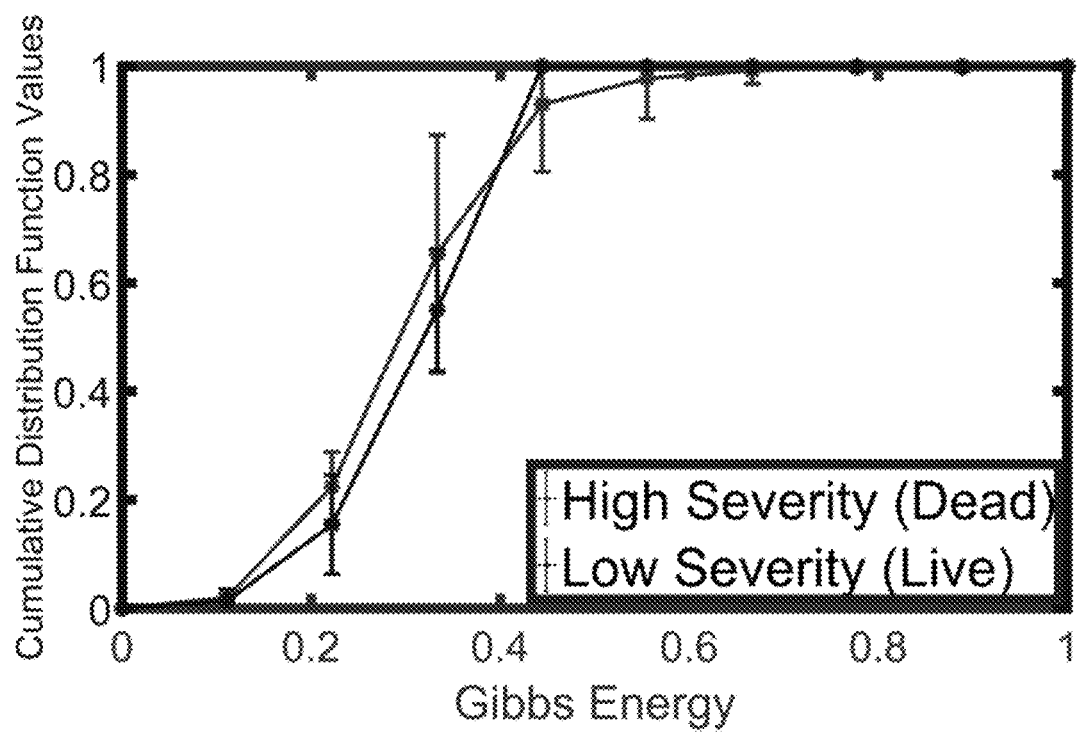
FIG. 6A is a graph comparing CDF values over Gibbs energy at radius $v_1$ for a subject with a high severity lung infection and a subject with a low severity lung infection.
Figure 6B:
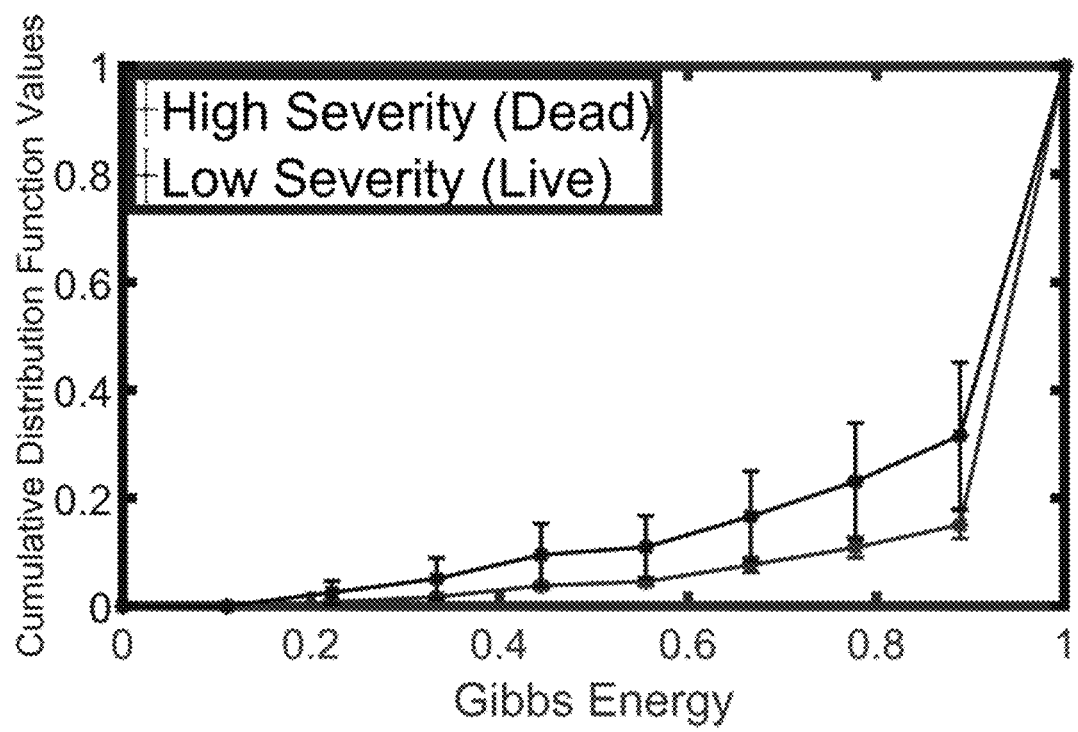
FIG. 6B is a graph comparing CDF values over Gibbs energy at radius $v_2$ for the subject with a high severity lung infection and the subject with a low severity lung infection of FIG. 6A.
Figure 6C:
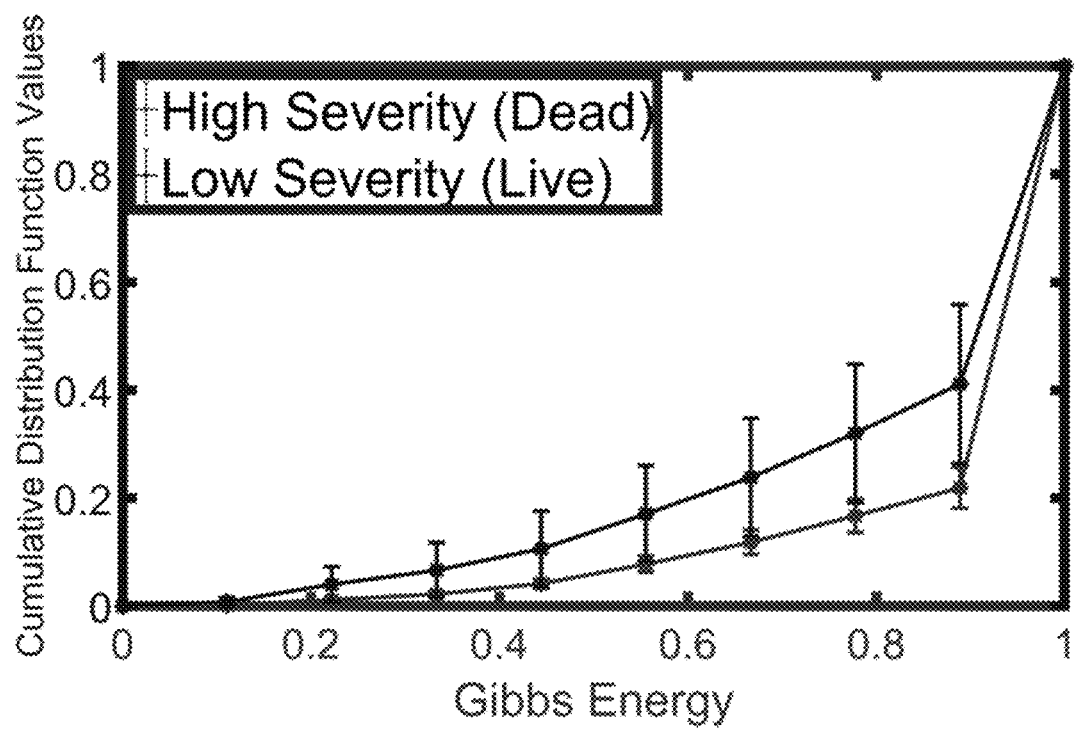
FIG. 6C is a graph comparing CDF values over Gibbs energy at radius $v_3$ for the subject with a high severity lung infection and the subject with a low severity lung infection of FIG. 6A.

Referring now to FIGS. 4A-4D, the figures illustrate the estimated Gibbs energy for high severity lung infections (top panels) and low severity lung infections (bottom panels). Gibbs energy calculated at three radii ($v_1$ in FIG. 4B, $v_2$ in FIG. 4C, and $v_3$ in FIG. 4D) is depicted as a color map fused over the x-ray images. These figures illustrate that the Gibbs energy in cases of high severity of COVID-19 pneumonia is high compared with the Gibbs energy for low-severity COVID-19 pneumonia. Since the collected X-ray images have different resolutions, CDF is used as a new scale-invariant representation to the estimated Gibbs energy which makes it suitable for all data collection protocols as shown in FIGS. 5A-5C. Referring now to FIGS. 6A-6C the average CDFs are calculated with a demonstration of the standard deviation at each point for both classes (high severity vs. low severity) to highlight the advantage of the proposed Gibbs energy as a new discriminatory image marker. The CDFs are rather distinctive which allows for straightforward classification by the proposed NN-based classifier. The output of the CAD system was an assessment of the severity of pneumonia in COVID-19 patients with two possible states: a first state indicating a low severity of infection ("low") or a second state indicating a high severity of infection ("high"). This was compared to the ground truth of the 200 clinical cases collected, 100 of which were from patients who died of COVID-19 and 100 of which recovered. Accurate system outputs include an assessment of "low" in a case that recovered and an output of "high" in a case that died. To confirm the accuracy of the proposed NN classification and fusion system, leave-one-subject-out (LOSO), 10-fold, 4-fold, and a 2-fold cross-validation approaches are performed on our datasets as demonstrated in Table 1. The following objective metrics are used to measure the accuracy of the proposed NN-based fusion system: (i) sensitivity, (ii) specificity, (iii) accuracy, and (iv) Dice similarity coefficient (DSC). As demonstrated in Table 1, the proposed system has achieved 100% accuracy with the LOSO validation test and 98.00%±2.00% for a 2-fold validation test (real-life scenario), all of which confirm the efficacy of the CAD system.

TABLE 1

| | Diagnostic accuracy of the CAD system | | | |
|---|---|---|---|---|
| | Sensitivity | Specificity | DSC | Accuracy |
| | Performance of the CAD System | | | |
| LOSO | 100% ± 0.00 | 100% ± 0.00 | 100% ± 0.00 | 100% ± 0.00 |
| 10-Fold | 100% ± 0.00 | 99% ± 1.00 | 99.50% ± 0.50 | 99.50% ± 0.50 |
| 4-Fold | 100% ± 0.00 | 98% ± 2.00 | 99% ± 1.00 | 99% ± 1.00 |
| 2-Fold | 100% ± 0.00 | 97% ± 3.00 | 98% ± 2.00 | 98% ± 2.00 |

TABLE 1-continued

Diagnostic accuracy of the CAD system

| | Sensitivity | Specificity | DSC | Accuracy |
|---|---|---|---|---|
| Performance of the CAD System when using only the Estimated Energy at $v_1$ | | | | |
| LOSO | 76% ± 4.29 | 96% ± 1.97 | 75% ± 4.27 | 86% ± 2.37 |
| 10-Fold | 74% ± 1.26 | 98% ± 4.21 | 83.61% ± 9.15 | 86% ± 7.37 |
| 4-Fold | 71% ± 8.28 | 98% ± 2.31 | 81.87% ± 5.05 | 84.50% ± 3.41 |
| 2-Fold | 71% ± 4.24 | 99% ± 1.41 | 80.87% ± 2.14 | 80.30% ± 1.41 |
| Performance of the Proposed CAD System when using only the Estimated Energy at $v_2$ | | | | |
| LOSO | 81% ± 3.94 | 94% ± 2.39 | 79.33% ± 3.93 | 87.5% ± 2.28 |
| 10-Fold | 79% ± 1.29 | 94% ± 5.07 | 85.45% ± 6.23 | 87% ± 4.83 |
| 4-Fold | 80% ± 8.86 | 93% ± 6.31 | 83.83% ± 6.15 | 86.50% ± 3.41 |
| 2-Fold | 77% ± 1.41 | 91% ± 2.82 | 82.16% ± 2.20 | 85.50% ± 2.12 |
| Performance of the Proposed CAD System when using only the Estimated Energy at $v_3$ | | | | |
| LOSO | 97% ± 1.71 | 94% ± 2.39 | 95% ± 1.85 | 95.5% ± 1.43 |
| 10-Fold | 93% ± 8.23 | 97% ± 4.83 | 94.78% ± 5.56 | 95% ± 5.27 |
| 4-Fold | 92% ± 1.13 | 95% ± 3.83 | 93.16% ± 7.82 | 93.50% ± 7.19 |
| 2-Fold | 91% ± 7.07 | 95% ± 1.41 | 92.79% ± 3.20 | 93% ± 2.82 |

An NN-based classifier was constructed using the estimated Gibbs energy at each radius to highlight the contribution of each Gibbs energy at each radius. As is clear from Table 1, the NN-classifier based on the estimated Gibbs energy at $v_3$ demonstrates the highest accuracy compared with the classification accuracies based on the estimated Gibbs energy at $v_2$ and $v_1$. Also, fusing the three estimated Gibbs energies by using the NN-Based classification system achieves higher accuracy compared with classification accuracies based on each single estimated Gibbs energy. The accuracy of the proposed NN-based fusion system is further compared with support vector machine (SVM), random forest, naive Bayes, K-nearest neighbors (KNN), and decision trees classifiers. The results shown in Table 2, when compared to those shown in Table 1, illustrate that the NN-based classification and fusion system disclosed herein has achieved the highest sensitivity, specificity, DSC, and accuracy compared with other approaches.

TABLE 2

Diagnostic accuracy using different classification systems.

| | Sensitivity | Specificity | DSC | Accuracy |
|---|---|---|---|---|
| SVM-Based CAD System | | | | |
| LOSO | 86% ± 3.48 | 94% ± 2.39 | 84% ± 3.49 | 90% ± 2.01 |
| 10-Fold | 78% ± 9.19 | 97% ± 4.83 | 85.96% ± 6.06 | 87.50% ± 4.86 |
| 4-Fold | 85% ± 1.41 | 92% ± 5.65 | 88.11% ± 1.76 | 88.50% ± 2.20 |
| 2-Fold | 83% ± 3.82 | 91% ± 3.83 | 86.44% ± 1.29 | 87% ± 1.15 |
| Random Forest-Based CAD System | | | | |
| LOSO | 76% ± 4.29 | 96% ± 1.97 | 75% ± 4.27 | 86% ± 2.37 |
| 10-Fold | 74% ± 1.26 | 98% ± 4.21 | 83.61% ± 9.15 | 86% ± 7.37 |
| 4-Fold | 71% ± 8.28 | 98% ± 2.31 | 81.87% ± 5.05 | 84.50% ± 3.41 |
| 2-Fold | 71% ± 4.24 | 99% ± 1.41 | 80.87% ± 2.14 | 80.30% ± 1.41 |
| Naive Bayes-Based CAD System | | | | |
| LOSO | 84% ± 3.68 | 94% ± 2.38 | 82.33% ± 3.68 | 89% ± 2.19 |
| 10-Fold | 80% ± 1.05 | 97% ± 4.83 | 87.13% ± 7.10 | 88.50% ± 5.79 |
| 4-Fold | 77% ± 6.00 | 97% ± 2.00 | 85.46% ± 4.36 | 87% ± 3.46 |
| 2-Fold | 77% ± 4.24 | 95% ± 1.41 | 84.58% ± 2.03 | 86% ± 1.41 |
| KNN-Based CAD System | | | | |
| LOSO | 80% ± 4.02 | 99% ± 1.00 | 79.66% ± 4.01 | 89.50% ± 2.04 |
| 10-Fold | 75% ± 8.87 | 100% ± 0.00 | 85.49% ± 5.88 | 87.50% ± 4.43 |
| 4-Fold | 71% ± 1.10 | 100% ± 0.00 | 82.61% ± 7.43 | 85.50% ± 5.50 |
| 2-Fold | 70% ± 0.00 | 100% ± 0.00 | 82.35% ± 0.00 | 85% ± 0.00 |
| Decision Trees-Based CAD System | | | | |
| LOSO | 80% ± 4.02 | 99% ± 1.00 | 79.66% ± 4.01 | 89.50% ± 2.04 |
| 10-Fold | 75% ± 8.87 | 100% ± 0.00 | 85.49% ± 5.88 | 87.50% ± 4.43 |
| 4-Fold | 71% ± 1.10 | 100% ± 0.00 | 82.61% ± 7.43 | 85.50% ± 5.50 |
| 2-Fold | 70% ± 0.00 | 100% ± 0.00 | 82.35% ± 0.00 | 85% ± 0.00 |

Automation

One or more steps in the method 10 may be implemented in an automated fashion, utilizing a computer or other electronic device to implement such steps. An exemplary apparatus within which various steps from method 10 may be implemented may be a server or multi-user computer that is coupled via a network to one or more client computers, as well as a medical imaging device. Each computer may represent practically any type of computer, computer system, data processing system or other programmable electronic device. Moreover, each computer may be implemented using one or more networked computers, e.g., in a cluster or other distributed computing system. In the alternative, the computer may be implemented within a single computer or other programmable electronic device, e.g., a desktop computer, a laptop computer, a handheld computer, a cell phone, a set top box, etc.

A computer typically includes a central processing unit including at least one microprocessor coupled to a memory, which may represent the random access memory (RAM) devices comprising the main storage of the computer, as well as any supplemental levels of memory, e.g., cache memories, non-volatile or backup memories (e.g., programmable or flash memories), read-only memories, etc. In addition, memory may be considered to include memory storage physically located elsewhere in the computer, e.g., any cache memory in a processor in the CPU, as well as any storage capacity used as a virtual memory, e.g., as stored on a mass storage device or on another computer coupled to this computer. The computer also typically receives a number of inputs and outputs for communicating information externally. For interface with a user or operator, a computer typically includes a user interface incorporating one or more user input devices (e.g., a keyboard, a mouse, a trackball, a joystick, a touchpad, and/or a microphone, among others) and a display (e.g., a CRT monitor, an LCD display panel, and/or a speaker, among others). Otherwise, user input may be received via another computer or terminal.

For additional storage, the computer may also include one or more mass storage devices, e.g., a floppy or other removable disk drive, a hard disk drive, a direct access storage device (DASD), an optical drive (e.g., a CD drive, a DVD drive, etc.), and/or a tape drive, among others. Furthermore, the computer may include an interface with one or more networks (e.g., a LAN, a WAN, a wireless network, and/or the Internet, among others) to permit the communication of information with other computers and electronic devices. Other hardware environments are contemplated within the context of the invention.

The computer operates under the control of an operating system and executes or otherwise relies upon various computer software applications, components, programs, objects, modules, data structures, etc. Moreover, various applications, components, programs, objects, modules, etc. may also execute on one or more processors in another computer coupled to the computer via a network, e.g., in a distributed or client-server computing environment, whereby the processing required to implement the functions of a computer program may be allocated to multiple computers over a network.

As an example, the computer may include a CAD system program used to implement one or more of the steps described above in connection with method 10. For the purposes of implementing such steps, an image database storing medical image data may be implemented in the computer. It will be appreciated, however, that some steps in method 10 may be performed manually and with or without the use of a computer.

DISCUSSION AND CONCLUSION

ARDS is the most common and severe pulmonary complication in COVID-19 patients. It is an acute hypoxemic respiratory failure that requires oxygen and ventilation therapy including intubation and invasive ventilation. Clinically patients may have dyspnea, tachypnea (respiratory rate≥30 breaths per minute), decreased peripheral oxygen saturation $S_pO_2 \leq 93\%$, poor oxygenation with the ratio of the partial pressure of arterial oxygen to fraction of inspired oxygen $PaO_2/FiO_2 < 300$ mmHg, or lung infiltrates greater than 50% within 48 h. ARDS occurred in 20% of hospitalized patients and 61% of ICU patients in one study. ARDS occurs when capillaries in the lung leak fluid into the alveoli, thereby impairing gas exchange in the lung and reducing oxygen uptake into the systemic arterial circulation. The consequent decrease in blood oxygen levels can be directly life-threatening, leading to multi-organ failure. Respiratory support of COVID-19 may use invasive or non-invasive methods to force oxygen into the airways under pressure. Invasive ventilation uses an endotracheal tube to feed oxygen directly into the lungs. Non-invasive methods employ such devices as continuous positive airway pressure (CPAP) and oxygen hoods which do not involve use of an internal tube. Non-invasive methods are typically used in the management of less severe cases.

Despite being vital for supporting respiration in patients with ARDS, ventilators are in short supply in hospitals. According to Imperial College London, 30% of patients diagnosed with COVID-19 are strongly recommended to be admitted to the hospitals, with a significant fraction of those patients also requiring respiratory support. As the pandemic spreads across the world, many countries stopped exporting ventilators. The paucity of ventilators is even more acute in under developed and developing countries in South America, Asia, and Africa.

High-pressure ventilation may cause lung injury, also called barotrauma or ventilator-induced lung injury (VILI). Even non-invasive ventilation carries some risk, as stress and strain associated with high tidal volumes may cause patient self-induced lung injury (P-SILI). The additional inflammation due to VILI or P-SILI may lead to aggravation of pulmonary edema and worsening of the very respiratory distress that ventilation was intended to treat. There is also the risk of heart failure, hypervolemia, and multi organ dysfunction, alone or in combination. Unfortunately, COVID-19 patients who are admitted to the ICU and require mechanical ventilation show strikingly high rates of mortality, ranging from 50-97% early in the pandemic. A more recent study showed lower but still dramatic mortality rates of 36% in ICU patients requiring mechanical ventilation and 30% in all COVID-19 patients admitted to the ICU.

Accurate and rapid diagnosis of COVID-19 pneumonia severity is challenging for radiologists as the disease has rapidly spread across the globe. Based on the results demonstrated in this study, AI systems, especially those based on deep learning, are promising tools to assist initial screening by radiologists. It could decrease workload, improve diagnostic accuracy, and enable appropriate treatments and ventilation management of COVID-19 patients. In the case of a pandemic as we now face, medical resources are seriously strained and must be used as efficiently as possible. Rapid diagnosis and accurate prognosis are essential. The AI-based method shows great potential to quantify disease severity and could be used to inform treatment decision-making in patients with COVID-19. AI in concert with thoracic imaging and other clinical information (epidemiology, PCR, clinical symptoms, and laboratory indicators) can effectively improve clinical outcomes. AI can increase the utility of chest X-ray imaging beyond first-line diagnostic imaging and into the areas of risk stratification, monitoring of clinical course, and selection between management approaches, such as invasive vs. non-invasive ventilation, for COVID-19 patients. Multimodal data, be they clinical, epidemiological, or potentially molecular data, can by fused with imaging data in an AI framework to build systems to detect and treat COVID-19 patients and potentially to contain its spread.

The results herein demonstrate the feasibility of using AI with medical imaging data, such as thoracic X-ray imaging data, to determine the severity of lung infection in cases of COVID-19. Severity of pneumonia, as indicated by chest X-ray, correlates highly with mortality and thus this CAD system may be used to predict mortality in COVID-19 patients. While the specification discusses systems and methods using X-ray thoracic X-ray imaging data as input, it should be understood that other 2D and 3D medical imaging data may be used with the neural network-based diagnostic system and methods disclosed herein.

Various aspects of different embodiments of the present disclosure are expressed in paragraphs X1, X2, and X3 as follows:

X1. An embodiment of the present disclosure includes a method for assessing pulmonary function, comprising:

receiving medical image data that includes image data of at least one lung; segmenting image data of the at least one lung from other image data; modeling the segmented image data using a model with a central-symmetric system of pixel-pixel interactions; and classifying, using a neural network, pulmonary function as a first state or a second state based at least in part on the model.

X2. An further embodiment of the present disclosure includes a process for assessing pulmonary function, comprising: receiving medical image data that includes image data of at least one lung; segmenting image data of the at least one lung from other image data; modeling the segmented image data using a model with a central-symmetric system of pixel-pixel interactions; and classifying, using a neural network, pulmonary function as a first state or a second state based at least in part on the model.

X3. A further embodiment of the present disclosure includes a computer aided diagnostic system, comprising: at least one data processor; at least one memory; and program code stored on the at least one memory, the program code configured to be executed by the at least one processor to cause the at least one processor to: receive medical image data that includes image data of at least one lung, segment image data of the at least one lung from other image data, model the segmented image data using a model with a central-symmetric system of pixel-pixel interactions, and classify, using a neural network, pulmonary function as a first state or a second state based at least in part on the model.

Yet other embodiments include the features described in any of the previous paragraphs X1, X2, or X3 as combined with one or more of the following aspects:

Wherein pulmonary function is impaired by an infection.

Wherein the infection is a Coronaviridae infection.

Wherein the infection is COVID-19.

Wherein the first state is low severity infection and wherein the second state is high severity infection.

Wherein the first state is non-severe infection and wherein the second state is severe infection.

Further comprising segmenting the image data of the at least one lung into healthy regions and unhealthy regions, and wherein modeling the segmented image data comprises modeling the unhealthy regions.

Further comprising segmenting the image data of the at least one lung into uninfected regions and infected regions, and wherein modeling the segmented image data comprises modeling the infected regions.

Further comprising segmenting the image data of the at least one lung into healthy regions and unhealthy regions, and wherein the segmented image data is segmented image data of the unhealthy regions.

Wherein the unhealthy regions are infected regions.

Wherein the unhealthy regions are subject to Coronaviridae infection.

Wherein the program code is further configured upon execution to cause the at least one processor to: segment the image data of the at least one lung into healthy regions and unhealthy regions, and wherein the segmented image data is segmented image data of unhealthy regions.

Wherein the model is at least one of translation, rotation, and scale invariant.

Wherein the model is a MGRF model.

Wherein the classifying uses a plurality of neural networks, each with different input, and a fusion neural network which uses the output of the plurality of neural networks as input.

Wherein modeling the segmented image data includes designating neighborhood sets for a plurality of different radii.

Wherein the model with the central-symmetric system of pixel-pixel interactions includes designation of neighborhood sets for a plurality of different radii.

Wherein modeling the segmented image data includes designating neighborhood sets in a MGRF model for a plurality of different radii.

Wherein the modeling further comprises determining Gibbs energy for each of the plurality of different radii.

Wherein the program code is further configured upon execution to cause the at least one processor to: determine Gibbs energy for each of the plurality of different radii.

Wherein the classifying uses a plurality of neural networks, each receiving Gibbs energy from different radii as input, and a fusion neural network which uses the output of the plurality of neural networks as input.

Wherein the neural network is a plurality of neural networks, each configured to receive Gibbs energy from different radii as input, and a fusion neural network which uses the output of the plurality of neural networks as input.

Wherein the fusion neural network outputs the classification of first state or second state.

Wherein the Gibbs energy is received as input for each of the plurality of neural networks in the form of a cumulative distribution function.

The foregoing detailed description is given primarily for clearness of understanding and no unnecessary limitations are to be understood therefrom for modifications can be made by those skilled in the art upon reading this disclosure and may be made without departing from the spirit of the invention.

The invention claimed is:

1. A method for assessing pulmonary function, comprising:
   receiving medical image data that includes image data of at least one lung;
   segmenting image data of the at least one lung from other image data;
   modeling the segmented image data using a model with a central-symmetric system of pixel-pixel interactions; and
   classifying, using a neural network, pulmonary function as a first state or a second state based at least in part on the model;
   wherein modeling the segmented image data includes designating neighborhood sets for a plurality of different radii and determining Gibbs energy for each of the plurality of different radii; and
   wherein the classifying uses a plurality of neural networks, each receiving Gibbs energy from different radii as input, and a fusion neural network which uses the output of the plurality of neural networks as input.

2. The method of claim 1, wherein pulmonary function is impaired by an infection.

3. The method of claim 2, wherein the infection is a Coronaviridae infection.

4. The method of claim 2, wherein the first state is low severity infection and wherein the second state is high severity infection.

5. The method of claim 1, further comprising segmenting the image data of the at least one lung into healthy regions and unhealthy regions, and wherein modeling the segmented image data comprises modeling the unhealthy regions.

6. The method of claim 1, wherein the model is translation, rotation, and scale invariant.

7. The method of claim 1, wherein the Gibbs energy is received as input for each of the plurality of neural networks in the form of a cumulative distribution function.

8. A computer aided diagnostic system, comprising:
- at least one data processor;
- at least one memory; and
- program code stored on the at least one memory, the program code configured to be executed by the at least one processor to cause the at least one processor to:
  - receive medical image data that includes image data of at least one lung;
  - segment image data of the at least one lung from other image data;
  - model the segmented image data using a model with a central-symmetric system of pixel-pixel interactions, including designation of neighborhood sets for a plurality of different radii;
  - determine Gibbs energy for each of the plurality of different radii; and
  - classify, using a plurality of neural networks, each configured to receive Gibbs energy from different radii as input, and a fusion neural network which uses the output of the plurality of neural networks as input, pulmonary function as a first state or a second state based at least in part on the model.

9. The system of claim 8, wherein pulmonary function is impaired by an infection.

10. The system of claim 9, wherein the infection is a Coronaviridae infection.

11. The system of claim 9, wherein the first state is low severity infection and wherein the second state is high severity infection.

12. The system of claim 8, wherein the program code is further configured upon execution to cause the at least one processor to:
- segment the image data of the at least one lung into healthy regions and unhealthy regions, and wherein the segmented image data is segmented image data of unhealthy regions.

13. The system of claim 8, wherein the model is translation, rotation, and scale invariant.

14. The system of claim 8, wherein the Gibbs energy is received as input for each of the plurality of neural networks in the form of a cumulative distribution function.

* * * * *